(12) United States Patent
Tiwari et al.

(10) Patent No.: US 10,586,611 B2
(45) Date of Patent: Mar. 10, 2020

(54) SYSTEMS AND METHODS EMPLOYING MERGE TECHNOLOGY FOR THE CLINICAL DOMAIN

(71) Applicant: PerkinElmer Informatics, Inc., Waltham, MA (US)

(72) Inventors: Abhinav Tiwari, Kanpur Uttar Pradesh (IN); Chad Millen, Guelph (CA); Harold Miller-Koren, Stoney Creek (CA); Samuel James Campbell, Kitchener (CA); Stephen Menyhart, Guelph (CA)

(73) Assignee: PerkinElmer Informatics, Inc., Waltham, MA (US)

( * ) Notice: Subject to any disclaimer, the term of this patent is extended or adjusted under 35 U.S.C. 154(b) by 310 days.

(21) Appl. No.: 15/247,821

(22) Filed: Aug. 25, 2016

(65) Prior Publication Data
US 2018/0060537 A1   Mar. 1, 2018

(51) Int. Cl.
*G16H 10/20* (2018.01)
*G16H 40/63* (2018.01)
(Continued)

(52) U.S. Cl.
CPC .......... *G16H 10/20* (2018.01); *G06F 16/221* (2019.01); *G06F 16/2282* (2019.01);
(Continued)

(58) Field of Classification Search
CPC .. G16H 10/20; G16H 40/63; G06F 17/30315; G06F 17/30339; G06F 17/30398;
(Continued)

(56) References Cited

U.S. PATENT DOCUMENTS 6,356,901 B1 *  3/2002  MacLeod .............. G06F 16/254
7,054,823 B1     5/2006  Briegs et al.
(Continued)

FOREIGN PATENT DOCUMENTS

WO    WO-2018/038745 A1    3/2018
WO    WO-2018/038746 A1    3/2018

OTHER PUBLICATIONS

"How do HIPAA authorizations apply to an electronic health information exchange environment", Feb. 2016 (date via. The WayBack Machine), U.S. Department of Health & Human Services (Year: 2016).*

(Continued)

*Primary Examiner* — Jason S Tiedeman
*Assistant Examiner* — Rachel F Durnin
(74) *Attorney, Agent, or Firm* — Banner & Witcoff, Ltd.

(57) ABSTRACT

Presented herein are systems and methods for merging and manipulating data from different sources of clinical trial data. Clinical trial data is collected using multiple different 'forms' and can be from either a single clinical trial or from multiple clinical trials. In certain embodiments, the systems and methods described herein are provided in the form of an intuitive graphical user interface (GUI) that enables a user to merge and manipulate data from two or more source tables of clinical trial data associated with one or more clinical studies to produce a custom merged table, without having to rely upon complex computer code.

29 Claims, 19 Drawing Sheets

(51) Int. Cl.
*G06F 16/22* (2019.01)
*G06F 16/242* (2019.01)
*G06F 19/00* (2018.01)

(52) U.S. Cl.
CPC ........ *G06F 16/2428* (2019.01); *G06F 19/324* (2013.01); *G16H 40/63* (2018.01)

(58) Field of Classification Search
CPC ........ G06F 19/00; G06F 19/30; G06F 19/324; G06F 7/16; G06F 7/32; G06F 7/14; G06K 15/1889
USPC ........................................................ 705/2–3
See application file for complete search history.

(56) References Cited

U.S. PATENT DOCUMENTS

| | | | | |
|---|---|---|---|---|
| 7,908,266 | B2* | 3/2011 | Zeringue | G06F 3/0481 707/714 |
| 9,633,076 | B1* | 4/2017 | Morton | G06F 16/248 |
| 9,842,151 | B2 | 12/2017 | Wang et al. | |
| 2002/0188475 | A1* | 12/2002 | Banta | G06F 19/321 705/3 |
| 2003/0055830 | A1 | 3/2003 | Gutierrez-Rivas et al. | |
| 2004/0243439 | A1 | 12/2004 | Huggard et al. | |
| 2005/0182657 | A1 | 8/2005 | Abraham-Fuchs et al. | |
| 2006/0224421 | A1 | 10/2006 | St. Ores et al. | |
| 2007/0067711 | A1 | 3/2007 | Woodall et al. | |
| 2007/0250779 | A1* | 10/2007 | Wallach | G06Q 50/22 715/740 |
| 2008/0256128 | A1 | 10/2008 | Pierce et al. | |
| 2010/0228699 | A1 | 9/2010 | Webber et al. | |
| 2013/0144790 | A1 | 6/2013 | Clements | |
| 2013/0151537 | A1* | 6/2013 | Woody | G06F 16/26 707/748 |
| 2014/0279972 | A1* | 9/2014 | Singh | G06F 16/215 707/694 |
| 2015/0081718 | A1 | 3/2015 | Schmidt | |
| 2016/0275121 | A1* | 9/2016 | Dave | G06F 16/2282 |
| 2017/0124153 | A1* | 5/2017 | Champlin | G06F 16/2365 |
| 2017/0193036 | A1* | 7/2017 | Yueh | G06F 16/2428 |
| 2018/0046779 | A1 | 2/2018 | Millen et al. | |
| 2018/0060538 | A1 | 3/2018 | Tiwari et al. | |

OTHER PUBLICATIONS

Annonymous, Joint (SQL), Wikopedia, 14 pages (2016).
International Search Report, PCT/US2016/049792, 3 pages, dated Mar. 15, 2017.
Written Opinion, PCT/US2016/049792, 11 pages, dated Mar. 15, 2017.
Cassells, S. et al., Case Report Tabulation Data Definition Specification (define.xml), CDISC, 45 pages (2003-2004).
CDISC Submission Data Standards Team, Study Data Tabulation Model, Version 1.4, CDISC, 40 pages (2013).
CDISC, Specification for the Operational Data Model (ODM), 54 pages, (2006) retieved on Oct. 21, 2016 _ <http://www.cdisc.org/system/files/all/generic/application/octet-stream/odm1_3_0_final.htm>.
CDISC, Study Data Tabulation Model (SDTM), Standard Overview, 3 pages, (2016) retrieved on Oct. 21, 2016, <http://www.cdisc.org/standards/foundational/sdtm>.
Graebner, R. W., Practical methods for Creating CDISC SDTM Domain Data Sets from Existing Data, SAS Global Forum, Pharma, Life Science and Healthcare, 11 pages (2008).
Hangfire, Job Control Documentation, 5 pages, retrieved on Oct. 21, 2016, <http://docs.hangfire.io/en/latest/>.
Iavindrasana, J. et al., Clinical Data Mining: a Review, IMIA and Schattauer GmbH, 13 pages(2009).
Medidata Rave: Unified EDC & CDMS Solution | Medidata Solutions, 4 pages, retrieved Oct. 21, 2016 on <https://www.mdsol.com/en/what-we-do/data-capture/medidata-rave>.
Medidata, Capturing the Value of EDC, medidata, 19 pages (2013).
OHDSI, Data Standardization, OHDSI, 3 pages, retrieved Oct. 21, 2016 <http://www.ohdsi.org/data-standarization/>.
Oracle Health Sciences Inform, Oracle Inform Overview, 2 pages, retrieved from on Oct. 21, 2016<http://www.oracle.com/us/products/applications/health-sciences/e-clinical/inform/index.html>.
Oracle Health Sciences, Oracle Health Sciences Inform: Comprehensive Clinical Data Caputer and Management Cloud, Oracle, 12 pages (2015).
Rave Web Services, A Valid ODM 1.3 Transactional Document, 1 page, retrieved on Oct. 21, 2016, <http://rws-webhelp.s3.amazonaws.com/WebHelp_ENG/features/common/01_valid_odm_%20transactional_document.html#valid-odm-transactional-document <http://rws-webhelp.s3.amazonaws.com/WebHelp_ENG/features/common/01_valid_odm_%20transactional_document.html>.
Rave Web Services, A Vlaid ODM 1.3 Snapshot Document, 1 page, retrieved Oct. 21, 2016, <http://rws-webhelp.s3.amazonaws.com/WebHelp_ENG/features/common/02_valid_odm_%20snapshot_document.html#valid-odm-snapshot-document <http://rws-webhelp.s3.amazonaws.com/WebHelp_ENG/features/common/02_valid_odm_%20snapshot_document.html>.
Rave Web Services, Complex formats, 2 pages (2014), retrieved on Oct. 21, 2016, <http://rws-webhelp.s3.amazonaws.com/WebHelp_ENG/features/12_configurable_datasets/03_complex_rendering.html#cds-complex-rendering <http://rws-webhelp.s3.amazonaws.com/WebHelp_ENG/features/12_configurable_datasets/03_complex_rendering.html>.
Rave Web Services, ODM Schema, 3 pages (2014), retrieved on Oct. 21, 2016, <http://rws-webhelp.s3.amazonaws.com/WebHelp_ENG/features/common/03_odm_schema.html>.
Rave Web Services, Using ODM, 4 pages (2014), retrieved on Oct. 21, 2016, <http://rws-webhelp.s3.amazonaws.com/WebHelp_ENG/introduction/using_odm.html#vendor-extensions <http://rws-webhelp.s3.amazonaws.com/WebHelp_ENG/introduction/using_odm.html>.
SAS and Pharmaceutical Executive, Rethinking Clinical Trials Data Integration, SAS, 5 pages (2009).
SAS, Fact Sheet, Clinical Data Integration, 4 pages (2014).
SAS, SAS® Clinical Data Integration, 6 pages, retrieved on Oct. 21, 2016, <http://www.sas.com/en_ph/industry/life-sciences/clincial-data-integration.html>.
Sparks, I., rwslib Documentation, Release 1.1.5, Rave Web Services, 72 pages (2016).
Stuelpner, J. and Shostak, J., Confessions of a Clinical Programmer: Creating SDTM Domains with SAS®, SAS, 19 pages, (2011).
Torres-Reyna, O., Merge/Append using R, Data & Statistical Services, Princeton University, 14 pages (2011).
WHO, Essential medicines and health products, Pharmacovigilance, 2 pages, retrieved on Oct. 21, 2016, <http://www.who.int/medicines/areas/quality_safety/safety_efficacy/pharmvigi/en/>.
Wikipedia, Data modeling, 8 pages, retrieved Oct. 21, 2016, <https://en.wikipedia.org/wiki/Data_modeling>.

* cited by examiner

SYSTEMS AND METHODS EMPLOYING MERGE TECHNOLOGY FOR THE CLINICAL DOMAIN

FIELD OF THE INVENTION

In certain embodiments, this invention relates generally to systems and methods for merging datasets comprising clinical trial data. More specifically, in certain embodiments, this invention relates to methods and systems for facilitating the creation of custom merged tables that combine clinical trial data from a variety of source types.

BACKGROUND OF THE INVENTION

Clinical trials require the collection, storage, analysis and reporting of large quantities of data. Clinical trial data includes not only the observations of disease progression and treatment effectiveness required to validate a new drug, but also data such as subject demographic information, operational data, and records of adverse side effects.

Clinical trial data is generally collected as a series of case report 'forms'. These forms are designed specifically for each study, based on the particular protocol(s) to be followed during the study. The case report forms specify the type of information, such as, for example, subject identification, physical measurements, test results, question and answer responses, etc., that are to be collected. These forms are typically filled out by, e.g. medical doctors, nurses, technicians, etc., at each subject visit or interaction.

Typically, different forms are designed to record different types of information. For example, a study protocol may specify a series of regularly scheduled subject visits, and, accordingly, a particular form for entering the data recorded from each visit, for each subject. Similarly, demographic information, such as subject age, ethnicity, gender, etc., may be recorded on a specific demographics form. In another example, an adverse events form may be used to record data related to any time a subject experiences an adverse side effect over the course of a study.

Recently, electronic data capture systems (EDC systems), such as Medidata Rave®, and Oracle® InForm, have been developed to provide a way to collect this clinical trial information electronically, rather than via paper forms. These systems allow for up-to-date forms, referred to as electronic case report forms (eCRF), for a particular study to be accessed and data to be entered into them electronically. The collected clinical trial data is thereby automatically stored in a database associated with the EDC System.

Once collected, however, the raw clinical trial data still needs to be analyzed and processed by a variety of stakeholders involved in the clinical trial sponsor organization (e.g. a pharmaceutical company), or otherwise associated with the sponsor organization. These stakeholders include a variety of personnel such as medical doctors, statisticians, and managers who are responsible for monitoring, analyzing, and reporting data collected over the course of the clinical trial. For example, medical doctors responsible for clinical development may need to review clinical trial data daily or weekly to assess drug efficacy and/or safety. Additionally, a sponsor organization may employ data scientists to carry out biostatistics analysis of results. In another example, stakeholders associated with pharmacovigilance monitoring must assess and report adverse event information to drug regulatory authorities.

Thus, clinical trial data is used by a variety of different stakeholders who perform a variety of different functions and, accordingly, may interact with different subsets of clinical trial data in different ways. In particular, stakeholders may need to analyze different subsets of data originating from one or more different types of eCRFs from one or more different clinical studies.

Thus, before beginning any advanced analysis of clinical trial data, stakeholders must perform a data consolidation process in order to extract and organize the particular clinical trial data that is relevant to their particular application. Portions of this clinical trial data may be spread across different eCRFs and/or different clinical studies. An integral part of this data consolidation process is the merging of different data sets retrieved from EDC, Clinical Trial Management Systems (CTMS), and Clinical Data Management Systems (CDMS) sources. Systems that retrieve clinical trial data from EDC (Electronic Data Capture) sources, CTMS (Clinical Trial Management Systems) sources, and/or CDMS (Clinical Data Management Systems) sources require the functionality to add, merge, modify, and process data from different datasets or one or more eCRFs from one or more clinical trial studies.

Providing systems and methods that are capable of addressing the need to merge this particular type of data obtained from different data sources pertaining to the clinical domain is non-trivial. Not only must such systems and methods enable data set merging in order to perform advanced analysis, but they must do so in a way that satisfies the diverse needs of a variety of stakeholders who may utilize several different systems for collecting, storing, and analyzing clinical data. In particular, the systems and methods for merging data should enhance the capabilities of existing clinical data collection or analysis systems, without requiring a change in their core functionality. Moreover, it is important that the systems and methods for merging clinical trial data are portable, such that they can readily be integrated within different clinical systems (e.g. different software applications that may be used to collect, store, and analyze clinical trial data). Approaches that are also platform-agnostic and can be therefore implemented and used with different platforms and technologies (e.g. different database systems, different types of computing devices) are also highly desirable. Pluggable architectures are advantageous, as they enable systems and methods that provide the ability to merge clinical trial data to be used within a variety of different client applications that may be familiar to different types of stakeholders.

Finally, there is a significant need for systems and methods for merging data sets that provide these capabilities in a user interface (UI) that does not require programming skills to use. Many stakeholders who work on or with clinical trial data do not have a background in programming and either must spend significant time and effort to accomplish data preparation tasks that require writing computer code, or rely on the support of programmers to prepare data before they can use it. Providing a powerful functionality to merge and manipulate clinical trial would enable many stakeholder who add significant value in aspects of clinical development such as reporting, analysis and decision making to perform their functions without facing a bottleneck in retrieving and preparing the data they use to accomplish their tasks.

Existing EDC and Clinical Data Management (CDMS) systems do not provide these capabilities. For example, systems such as Medidata Rave® capture, manage and provide patient data, but do not natively include functionality to merge data from two or more eCRFs. Similarly, systems such as Oracle® InForm also lack the functionality to merge two or more eCRFs (even if the eCRFs are from the same study). Finally, although commercial data integration systems provide functionalities to store and manage clinical data, including the ability to merge data from two data sets, they lack the requisite flexibility and user-friendliness described above. For example, current data integration systems are not pluggable to other systems and must be operated as stand-alone solutions.

Moreover, current systems do not provide an interactive user interface for defining complex data merging operations. Instead, for example, data merging processes in SAS® Clinical Data Integration System are defined by SAS® code. Accordingly, performing data merging operations requires a skilled SAS® programmer to write code. This forces stakeholders to either learn a complex programming language, or to rely on programmers in order to accomplish their data consolidation needs.

There exists, therefore, a need for systems and methods that provide a portable, platform-agnostic, pluggable data merging technology that enable a user merge data from different sources of clinical trial data in order to perform advanced analysis. Moreover, there is a need for systems and methods that provide, and enable a user to leverage this functionality without requiring the user to write complex computer code.

SUMMARY OF THE INVENTION

Presented herein are systems and methods for merging and manipulating data from different sources of clinical trial data. Clinical trial data is collected using multiple different 'forms' and can be from either a single clinical trial or from multiple clinical trials. In certain embodiments, the systems and methods described herein are provided in the form of an intuitive graphical user interface (GUI) that enables a user to merge and manipulate data from two or more source tables of clinical trial data associated with one or more clinical studies to produce a custom merged table, without having to rely upon complex computer code.

The underlying data sources from which a final merged table is produced vary in terms of the format in which the data values are stored, as well as how the data is represented according to a particular data model. Accordingly, the systems and methods presented herein are applicable to data originating from a variety of systems used to collect and manage clinical trial data, such as EDC systems, CTMS systems, and CDMS systems. Thus, the systems and methods presented herein may be applied in a larger system, as a tool that may be used as a powerful mechanism to merge data from different subsystems that are used to collect, store, and analyze clinical trial data. The systems and methods described herein thereby enable clinical trial data to be combined and manipulated to provide datasets (e.g. as a merged table) that can be used for advanced analysis by stakeholders such as medical doctors, statisticians, and managers who are responsible for monitoring, analyzing, and reporting data collected over the course of the clinical trial.

In the context of clinical trial data that is collected using forms (e.g. data collected as eCRFs via an EDC system), the technology provides a uniform merge methodology where the data originating from different sources of clinical trial data is converted to tabular format prior to producing a final merged table, irrespective of the data-field format (e.g. the specifications of different fields inside an eCRF) and the data source type (e.g. different eCRFs, such as an eCRF for recording demographics information, or an eCRF for recording an adverse event).

In certain embodiments, the systems and methods described herein are implemented as a web-application, or as a desktop-application using appropriate technologies (e.g. appropriate technologies for implementing a web application, such as appropriate web framework technologies (e.g. Django®, PHP), appropriate webpage design technologies (e.g. HTML, CSS, JavaScript®), e.g. appropriate technologies for implementing a desktop application such as Java™, C#). Accordingly, the systems and methods herein are not constrained to any particular platform, but rather are platform-agnostic.

Moreover, in certain embodiments, the systems and methods described herein are implemented as a plug-in that adds the features of the merge technology to an existing computer program, such as a client application.

Accordingly, the merge technology of the systems and methods described herein is not constrained to a particular implementation, and provides flexibility and portability allowing it to be used within different systems (e.g. different software applications) for managing clinical trial data.

Additionally, in certain embodiments, the technology puts no theoretical limitation on the number, and size of the source tables to be merged to produce a single custom merged table.

In certain embodiments, by providing the user with the ability to control the process of merging and manipulating source tables of clinical trial data associated with one or more clinical studies, the systems and methods herein allow a user to control the manner in which the source tables are merged in order to produce a custom merged table.

In particular, a custom merged table that is produced by merging two or more source tables combines data from each of the source tables into a final merged table. The particular data that is included in the final merged table, and how it is stored in the final merged table depends on the columns that are present in each of the source tables and how the columns from different source tables relate to each other.

For example, columns in a first source table that represent the same field as columns in a second source table are mapped to each other, such that each of one or more columns in the final merged table corresponds to the columns in the first and second source table that are mapped to each other (e.g. the corresponding column of the merged table represents the same field as the column in the first source table to which a column in the second source table is mapped). The corresponding column in the merged table stores the data values from the column in the first source table, as well as the values from the column in the second source table that is mapped to the column of the first source table.

In certain embodiments, the systems and methods described herein automatically determine that a name of a column of a first source table matches a name of a column in the second source table, and automatically map the column of the second source table to the matching column of the first source table.

In certain embodiments, a user may interact with the GUI to select columns in the second source table that were not previously mapped to any column in the first source table. The user may then select a column of the first source table to which the selected column of the second source will be mapped. Similarly, the user may select a column of the second source table that was automatically mapped to a column of the first source table and unmap the second column from the column of the first source table to which it was previously mapped.

In certain embodiments, the user may also identify columns that they do not want to include in the final merged table. Accordingly, the user may select one or more columns to be removed from the merged table. Similarly, the user may select columns that were previously removed from the merged table to be added to the merged table.

Additionally, in certain embodiments, the merge technology described herein enable a user to manipulate the data type of the values that are stored in the merged table. For example, following an initial user selection of a first source table, the systems and methods described herein may initially identify the column names of each of the columns in the first source table, and display, via the graphical user interface, the column names in a list of columns to be included in the merged table. The merge technology may also identify a data type that is used to store each of the values in a particular column, and for each column to be included in the merged table, display an indication of the data type that is used to store the values of that column (e.g. text that identifies a data type is displayed next to each column name, e.g. the text 'string' indicates a text data type, e.g. the text 'float' or 'int' indicates a numerical data type, e.g. the text 'date' indicates a date data type).

In certain embodiments, a user may change the data type of a column to be included in the merged table. In particular, a user may select a column to be included in the merged table, and select a new data type, such that when the merged table is created, the values that are stored in the selected column are converted from their original data type to the new data type (e.g. an integer may be converted to a string, e.g. a float may be converted to an integer) and stored as the new data type in the merged table.

In certain embodiments, the user may change the data type of a selected column to be included in the merged table that corresponds to a column in a first source table to which a column in a second source table is mapped. Accordingly, when the values from the corresponding column of the first source table are stored in the merged table, they are converted to the new data type, and stored as the new data type in the merged table. Similarly, the values of the column of the second source table that is mapped to the column of the first source table are also converted to the new data type, and stored as the new data type in the merged table.

In certain embodiments, a user may select a single source table, and change the data type of a selected column to be included in the merged table to a new data type. The user may then provide an input to the GUI instructing the processor to create a merged table from only the single source table. Accordingly, the merged table will comprise the data from the single source table, but with the values of the selected column stored as the new data type. This functionality enables a user to change the data type that is used to store data values belonging to an existing form that have been imported as a source table without merging the imported source table with another table.

Accordingly, by providing a the capability to merge and manipulate (e.g. change the data type of a column) clinical trial data stored in tabular format via an intuitive GUI, the systems and methods described herein enable users to combine and manipulate clinical trial data, and produce custom merged tables that comprise the specific clinical trial data that is relevant to their particular function without having to rely upon complex computer code. Thus, the systems and methods described herein thereby address a significant bottleneck in the analysis and reporting of clinical trial data.

In one aspect, the invention is directed to a method for merging two or more source tables of clinical trial data associated with one or more clinical studies to produce a custom merged table via a graphical user interface (GUI), the method comprising the steps of: (a) accessing, by a processor of a computing device, a plurality of available source tables; (b) providing, by the processor, for display on the GUI a list of the available source tables; (c) receiving, by the processor, a user selection of a first source table from the list of available source tables, wherein the first source table comprises n rows, such that each column of the first source table stores n values; (d) receiving, by the processor, a user selection of a second source table from the list of available source tables, wherein the second source table comprises m rows, such that each column of the second source table stores m values; (e) determining, by the processor, a set of columns to be included in a merged table, wherein each column in the set of columns corresponds to either a column of the first source table or a column of the second source table; (f) automatically mapping, by the processor, each of one or more columns of the second source table to a respective column in the first source table; (g) merging, by the processor, the first source table with the second source table to produce a merged table, wherein merging the first source table with the second source table comprises: for each column in the set of columns to be included in the merged table that corresponds to a column in the first source table to which a column of the second source table is mapped: storing each of then values from the column in the first source table in consecutive rows 1 through n of a corresponding column in the merged table; storing each of the m values from the column in the second source table that is mapped to the column of the first source table in consecutive rows (n+1) through (n+m) immediately following rows 1 through n of the corresponding column in the merged table; and (h) storing, by the processor, the merged table for further processing and/or retrieval by a client application.

In certain embodiments, determining the set of columns to be included a merged table comprises identifying the columns in the first source table, and for each identified column of the first source table, adding a corresponding column to the set of columns to be included in the merged table, such that each column in the set of columns to be included in the merged table initially corresponds to a column of the first source table.

In certain embodiments, automatically mapping one or more columns of the second source table comprises: determining, by the processor, that a name of a column of the first source table matches a name of a column of the second source table; and mapping, by the processor, the matching column of the second source table to the matching column of the first source table.

In certain embodiments, merging the first source table with the second source table comprises: for each column in the set of columns to be included in the merged table that corresponds to a column in the first source table to which no column in the second source table is mapped: storing each of the n values from the column in the first source table in n consecutive rows 1 through n of a corresponding column of the merged table, leaving immediately following consecutive rows (n+1) through (n+m) blank; and for each column in the set of columns to be included in the merged table that corresponds to a column in the second source table that is not mapped to a column in the first source table: storing each of the m data values from the column in the second source table in consecutive rows (n+1) through (n+m) of a corresponding column of the merged table immediately following rows 1 through n, leaving rows 1 through n blank.

In certain embodiments, the method comprises: in a first designated location of the GUI (e.g. a source tables pane), displaying a name of the first source table, and names of each of the columns in the first source table; also in the first designated location of the GUI (e.g. the source tables pane), displaying a name of the second source table, and names of each of the columns in the second source table that are mapped to a respective column in the first source table; and in a second designated location of the GUI (e.g. an unmatched columns pane), displaying a name of each of the columns in the second source table that are not mapped to any of the columns in the first source table.

In certain embodiments, the method comprises at least one of: (i) receiving, by the processor, a user selection of a column in the second source table that is not previously mapped to any of the columns in the first source table (e.g., not previously mapped because the name of the selected column of the second source table did not match the name of any column of the first source table and was not automatically mapped), and mapping the selected column of the second source table to a selected column in the first source table (e.g., wherein the selection of the column in the second source table is an initial click of a drag-and-drop procedure, and wherein the selection of the column in the first source table is a release of the drag-and-drop procedure); and (ii) receiving, by the processor, a user selection of a column in the second source table that is mapped to a respective column the first source table, and unmapping the selected column of the second source table from the respective column of the first source table.

In certain embodiments, the method comprises: in a designated location of the GUI (e.g. a merged table pane), displaying a name of each column in the set of columns to be included in the merged table; receiving, by the processor, a user selection of a column in the set of columns to be included in the merged table to be removed from the merged table; and removing the selected column from the set of columns to be included in the merged table.

In certain embodiments, the method comprises: displaying, in a designated location of the GUI (e.g. a merged table pane), displaying a name of each column in the set of columns to be included in the merged table, along with an indication of a corresponding data type, wherein the corresponding data type is a data type that will be used to store values in the column (e.g. text that identifies a data type is displayed next to each column name, e.g. the text 'string' indicates a text data type, e.g. the text 'float' or 'int' indicates a numerical data type, e.g. the text 'date' indicates a date data type).

In certain embodiments, the method comprises: receiving a user selection of a column to be included in the merged table from the designated location of the GUI (e.g. the merged table pane); receiving a user selection of a new data type (e.g. the user may click on the data type next to the column name and enter a new data type); and merging, by a processor of a computing device, the first source table with the second source table to produce a merged table, wherein merging the first source table with the second source table comprises converting each value to be stored in the selected column to the new data type prior to storing them in the merged table.

In certain embodiments, the first source table comprises data from a first study event and the second source table comprises data from a second study event that is distinct from the first study event. In certain embodiments, the first source table comprises data from a first clinical study and the second source table comprises data from a second clinical study that is distinct from the first clinical study.

In certain embodiments, each table of the plurality of available source tables comprises data recorded using a different form (e.g. an eCRF), wherein each form is a pre-defined template that identifies a set of data to be recorded during a study event of a clinical trial. In certain embodiments, each table of the plurality of available source tables comprises one or more form entries, each form entry comprising a set of clinical trial data recorded for a particular subject, at a particular study event, and using a particular form comprising a list of predefined fields for which data is collected.

In certain embodiments, at least one of the first source table and the second source table comprises operational data. In certain embodiments, the operational data comprises at least one member selected from the group consisting of an audit record, a query, a comment, and a signature. In certain embodiments, the operational data comprises an audit record. In certain embodiments, wherein the operational data comprises an electronic signature.

In certain embodiments, the method comprises automatically updating, by the processor, the merged table to reflect updates to the clinical trial data.

In another aspect, the invention is directed to a method for changing a data type of values stored in one or more columns of a source table of clinical trial data associated with one or more clinical studies via a graphical user interface (GUI), the method comprising: (a) accessing, by a processor of a computing device, a plurality of available source tables; (b) providing, by the processor, for display on the GUI a list of the available source tables; (c) receiving, by the processor, a user selection of a source table from the list of available source tables; (d) determining, by the processor, a set of columns to be included in a merged table, wherein each column in the set of columns corresponds to a column of the source table; (e) displaying, by the processor, in a first designated location of the GUI (e.g. a merged table pane) a name of each of the columns to be included in the merged table; (f) for each column to be included in the merged table, displaying, by the processor, an indication of a data type of the respective column; (g) receiving, by the processor, a user selection of a column to be included in the merged table; (h) receiving, by the processor, a user selection of a new data type of the selected column; (i) for each column to be included in the merged table, storing, by the processor, the values of the corresponding column of the source table in the respective column of the merged table, wherein storing the values of the column of the source table corresponding to the selected column comprises converting the values of the column of the source table corresponding to the selected column to the new data type, and storing the converted values in the merged table; and (j) storing, by the processor, the merged table for further processing and/or retrieval by a client application.

In certain embodiments, determining the set of columns to be included the merged table comprises identifying the columns in the source table, and for each identified column of the source table, adding a corresponding column to the set of columns to be included in the merged table, such that each column in the set of columns to be included in the merged table initially corresponds to a column of the source table.

In certain embodiments, the method comprises: in a designated location of the GUI (e.g. a merged table pane), displaying a name of each column in the set of columns to be included in the merged table; receiving, by the processor, a user selection of a column in the set of columns to be included in the merged table to be removed from the merged table; and removing the selected column from the set of columns to be included in the merged table.

In certain embodiments, each table of the plurality of available source tables comprises data recorded using a different form (e.g. an eCRF), wherein each form is a pre-defined template that identifies a set of data to be recorded during a study event of a clinical trial. In certain embodiments, each table of the plurality of available source tables comprises one or more form entries, each form entry comprising a set of clinical trial data recorded for a particular subject, at a particular study event, and using a particular form comprising a list of predefined fields for which data is collected.

In certain embodiments, the source table comprises operational data. In certain embodiments, the operational data comprises at least one member selected from the group consisting of an audit record, a query, a comment, and a signature. In certain embodiments, the operational data comprises an audit record. In certain embodiments, the operational data comprises an electronic signature.

In certain embodiments, the method comprises automatically updating, by the processor, the merged table to reflect updates to the clinical trial data.

In another aspect, the invention is directed to a system for merging two or more source tables of clinical trial data associated with one or more clinical studies to produce a custom merged table via a graphical user interface (GUI), the system comprising: a processor; and a memory having instructions stored thereon, wherein the instructions, when executed by the processor, cause the processor to: (a) access a plurality of available source tables; (b) provide for display on the GUI a list of the available source tables; (c) receive a user selection of a first source table from the list of available source tables, wherein the first source table comprises n rows, such that each column of the first source table stores n values; (d) receive a user selection of a second source table from the list of available source tables, wherein the second source table comprises m rows, such that each column of the second source table stores m values; (e) determine a set of columns to be included in a merged table, wherein each column in the set of columns corresponds to either a column of the first source table or a column of the second source table; (f) automatically map each of one or more columns of the second source table to a respective column in the first source table; (g) merge the first source table with the second source table to produce the merged table, wherein merging the first source table with the second source table comprises: for each column in the set of columns to be included in the merged table that corresponds to a column in the first source table to which a column of the second source table is mapped: storing each of the n values from the column in the first source table in consecutive rows 1 through n of a corresponding column in the merged table; storing each of the m values from the column in the second source table that is mapped to the column of the first source table in consecutive rows (n+1) through (n+m) immediately following rows 1 through n of the corresponding column in the merged table; and (h) store the merged table for further processing and/or retrieval by a client application.

In certain embodiments, the system is a plug-in architecture.

In certain embodiments, the instructions cause the processor to determine the set of columns to be included a merged table by: identifying the columns in the first source table; and for each identified column of the first source table, adding a corresponding column to the set of columns to be included in the merged table, such that each column in the set of columns to be included in the merged table initially corresponds to a column of the first source table.

In certain embodiments, the instructions cause the processor to automatically map one or more columns of the second source table by: determining that a name of a column of the first source table matches a name of a column of the second source table; and mapping the matching column of the second source table to the matching column of the first source table.

In certain embodiments, the instructions cause the processor to merge the first source table with the second source table by: for each column in the set of columns to be included in the merged table that corresponds to a column in the first source table to which no column in the second source table is mapped: storing each of the n values from the column in the first source table inn consecutive rows 1 through n of a corresponding column of the merged table, leaving immediately following consecutive rows (n+1) through (n+m) blank; and for each column in the set of columns to be included in the merged table that corresponds to a column in the second source table that is not mapped to a column in the first source table: storing each of them data values from the column in the second source table in consecutive rows (n+1) through (n+m) of a corresponding column of the merged table immediately following rows 1 through n, leaving rows 1 through n blank.

In certain embodiments, the instructions cause the processor to: in a first designated location of the GUI (e.g. a source tables pane), display a name of the first source table, and names of each of the columns in the first source table; also in the first designated location of the GUI (e.g. the source tables pane), display a name of the second source table, and names of each of the columns in the second source table that are mapped to a respective column in the first source table; and in a second designated location of the GUI (e.g. an unmatched columns pane), display a name of each of the columns in the second source table that are not mapped to any of the columns in the first source table.

In certain embodiments, the instructions cause the processor to perform at least one of the following: (i) receive a user selection of a column in the second source table that is not previously mapped to any of the columns in the first source table (e.g., not previously mapped because the name of the selected column of the second source table did not match the name of any column of the first source table and was not automatically mapped), and map the selected column of the second source table to a selected column in the first source table (e.g., wherein the selection of the column in the second source table is an initial click of a drag-and-drop procedure, and wherein the selection of the column in the first source table is a release of the drag-and-drop procedure); and (ii) receive a user selection of a column in the second source table that is mapped to a respective column the first source table, and unmapping the selected column of the second source table from the respective column of the first source table.

In certain embodiments, the instructions cause the processor to: in a designated location of the GUI (e.g. a merged table pane), display a name of each column in the set of columns to be included in the merged table; receive a user selection of a column in the set of columns to be included in the merged table to be removed from the merged table; and remove the selected column from the set of columns to be included in the merged table.

In certain embodiments, the instructions cause the processor to: in a designated location of the GUI (e.g. a merged table pane), display a name of each column in the set of columns to be included in the merged table, along with an indication of a corresponding data type, wherein the corresponding data type is a data type that will be used to store values in the column (e.g. text that identifies a data type is displayed next to each column name, e.g. the text 'string' indicates a text data type, e.g. the text 'float' or 'int' indicates a numerical data type, e.g. the text 'date' indicates a date data type).

In certain embodiments, the instructions cause the processor to: receive a user selection of a column to be included in the merged table from the designated location of the GUI (e.g. the merged table pane); receive a user selection of a new data type (e.g. the user may click on the data type next to the column name and enter a new data type); and merge the first source table with the second source table to produce a merged table, wherein merging the first source table with the second source table comprises converting each value to be stored in the selected column to the new data type prior to storing them in the merged table.

In certain embodiments, the first source table comprises data from a first study event and the second source table comprises data from a second study event that is distinct from the first study event. In certain embodiments, the first source table comprises data from a first clinical study and the second source table comprises data from a second clinical study that is distinct from the first clinical study.

In certain embodiments, each table of the plurality of available source tables comprises data recorded using a different form (e.g. an eCRF), wherein each form is a pre-defined template that identifies a set of data to be recorded during a study event of a clinical trial. In certain embodiments, each table of the plurality of available source tables comprises one or more form entries, each form entry comprising a set of clinical trial data recorded for a particular subject, at a particular study event, and using a particular form comprising a list of predefined fields for which data is collected.

In certain embodiments, at least one of the first source table and the second source table comprises operational data. In certain embodiments, the operational data comprises at least one member selected from the group consisting of an audit record, a query, a comment, and a signature. In certain embodiments, the operational data comprises an audit record. In certain embodiments, wherein the operational data comprises an electronic signature.

In certain embodiments, the instructions cause the processor to automatically update the merged table to reflect updates to the clinical trial data.

In another aspect, the invention is directed to a system for changing a data type of values stored in one or more columns of a source table of clinical trial data associated with one or more clinical studies via a graphical user interface (GUI), the system comprising: a processor; and a memory having instructions stored thereon, wherein the instructions, when executed by the processor, cause the processor to: (a) access a plurality of available source tables; (b) providing for display on the GUI a list of the available source tables; (c) receive a user selection of a source table from the list of available source tables; (d) determine a set of columns to be included in a merged table, wherein each column in the set of columns corresponds to a column of the first source table; (e) display in a first designated location of the GUI (e.g. a merged table pane) a name of each of the columns to be included in the merged table; (f) for each column to be included in the merged table, display an indication of a data type of the respective column; (g) receive a user selection of a column to be included in the merged table; (h) receive a user selection of a new data type of the selected column; (i) for each column to be included in the merged table, store the values of the corresponding column of the source table in the respective column of the merged table, wherein storing the values of the column of the source table corresponding to the selected column comprises converting the values of the column of the source table corresponding to the selected column to the new data type, and storing the converted values in the merged table; and (j) store the merged table for further processing and/or retrieval by a client application.

In certain embodiments, the system is a plug-in architecture.

In certain embodiments, the instructions cause the processor to determine the set of columns to be included the merged table by: identifying the columns in the source table, and for each identified column of the source table, adding a corresponding column to the set of columns to be included in the merged table, such that each column in the set of columns to be included in the merged table initially corresponds to a column of the source table.

In certain embodiments, the instructions cause the processor to: in a designated location of the GUI (e.g. a merged table pane), display a name of each column in the set of columns to be included in the merged table; receive a user selection of a column in the set of columns to be included in the merged table to be removed from the merged table; and remove the selected column from the set of columns to be included in the merged table.

In certain embodiments, each table of the plurality of available source tables comprises data recorded using a different form (e.g. an eCRF), wherein each form is a pre-defined template that identifies a set of data to be recorded during a study event of a clinical trial. In certain embodiments, each table of the plurality of available source tables comprises one or more form entries, each form entry comprising a set of clinical trial data recorded for a particular subject, at a particular study event, and using a particular form comprising a list of predefined fields for which data is collected.

In certain embodiments, the source table comprises operational data. In certain embodiments, the operational data comprises at least one member selected from the group consisting of an audit record, a query, a comment, and a signature. In certain embodiments, the operational data comprises an audit record. In certain embodiments, the operational data comprises an electronic signature.

In certain embodiments, the instructions cause the processor to automatically update the merged table to reflect updates to the clinical trial data.

BRIEF DESCRIPTION OF THE FIGURES

The foregoing and other objects, aspects, features, and advantages of the present disclosure will become more apparent and better understood by referring to the following description taken in conjunction with the accompanying drawings, in which.

Figure 1:
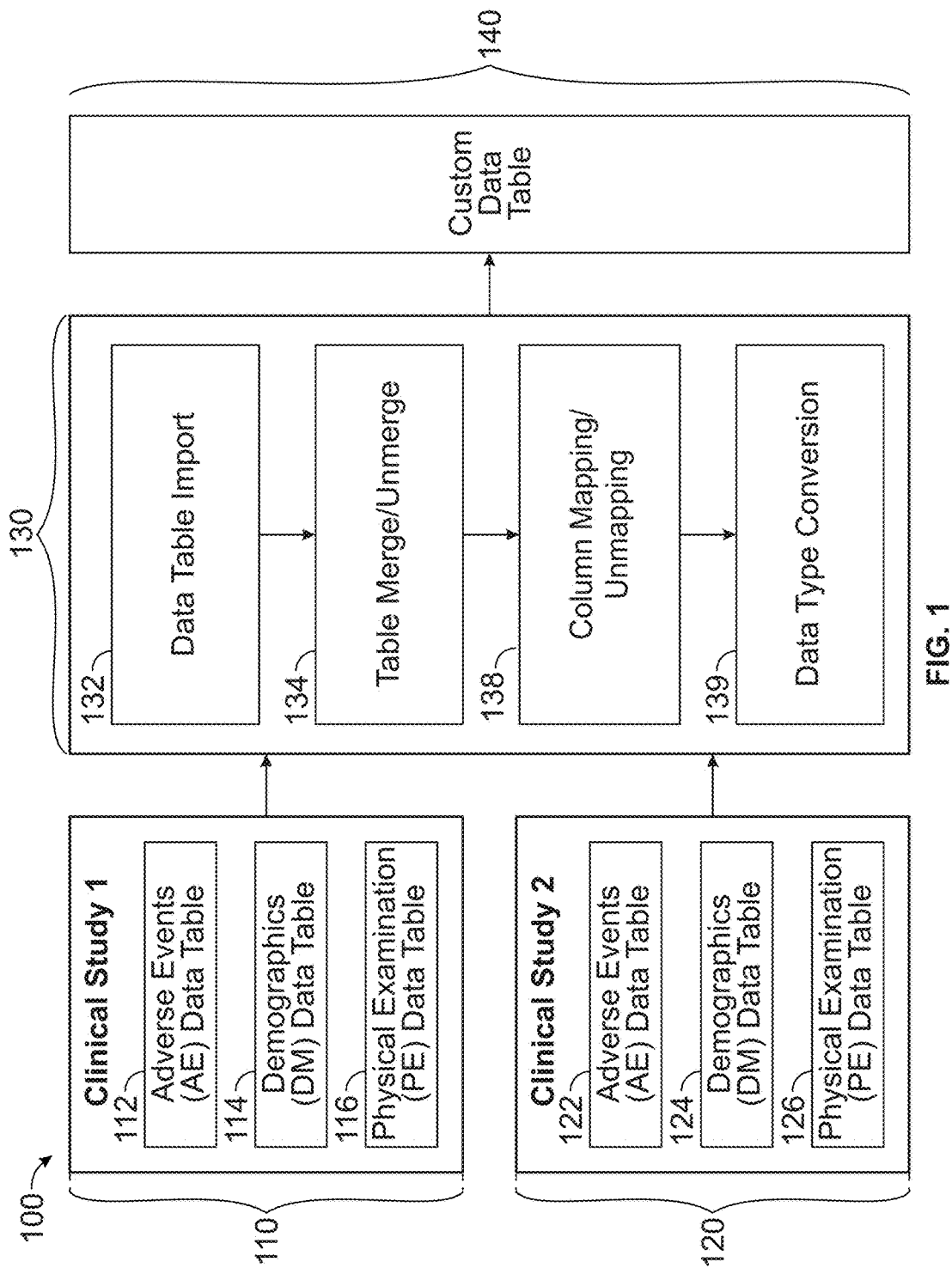
FIG. 1 is a block flow diagram showing the organization of components and subsystems associated with a merge technology system architecture, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

Definitions

Clinical Study, Clinical Trial: As used herein, the terms "clinical trial," "clinical study," and "study," refer to research studies that test, for example, how well new medical approaches work in human subjects. The number of subjects is typically governed by the duration and type of the study. Clinical trial data includes, without limitation, operational data and clinical data, as well as other data collected and managed over the course of a clinical trial, such as data that relates to the management and planning of a clinical trial and financial data. For example, data related to clinical trial and site planning, the management of investigators conducting the clinical trial, study financials and payment management, as well as supply tracking are collected and used for monitoring and decision making purposes throughout a clinical trial. Clinical trial data also includes additional data from outside sources, such as public data sources (e.g. electronic medical records, and administrative claims data) that may be used in combination with the recorded clinical data in order to analyze clinical data (e.g. to compare the efficacy of the drug under test with existing treatments, e.g. to make predictions with regard to how the drug under test may perform in combination with existing treatments).

Subject: As used herein, the term "subject" refers to a human subject (e.g. a patient) in a clinical trial.

Study events: As used herein, the term "study event" refers to any of one or more events occurring over the course of a clinical trial that results in the collection of clinical trial data for one or more different subjects. Each study event differs from other study events in terms of the purpose of the study event, and, accordingly, the different electronic case report forms (eCRFs) that are used to collect the clinical trial data for that event. The number and types of study events are defined during the clinical trial design.

Electronic Data Capture (EDC): As used herein, the terms "electronic data capture," and "EDC" refer to the process of recording and storing clinical trial data electronically. Clinical trial data is generally collected as a series of case report forms (CRFs). The CRFs are designed specifically for each study, based on the particular protocol(s) to be followed during the study. The CRFs specify the type of information, such as, for example, subject identification, physical measurements, test results, question and answer responses, etc., that are to be collected. These forms are typically filled out by, e.g. medical doctors, nurses, technicians, etc., at each study event for a particular subject (e.g. a subject visit to a doctor, or other interaction, such as reporting demographics information). In an EDC process, the CRFs are electronic forms (eCRFs) and data is entered into them electronically (e.g. on a computer, or a mobile device). Once entered, the data for each individual form (e.g. the particular form containing the data for a given study event and subject) is stored electronically.

Form: As used herein, the term "form" refers to a predefined template (e.g. a case report form as used in a clinical trial, e.g. an eCRF) that identifies a set of data to be recorded during a study event. A form is analogous to a page in a paper CRF book or an electronic CRF (eCRF) screen.

In certain embodiments, a form comprises a list of fields (e.g. age, weight, race, gender, blood pressure, cholesterol levels, hemoglobin levels) for which values are to be collected for each subject during a specific study event. The fields belonging to a particular form are typically logically or temporally related. For example, a demographics form may list fields such as age, gender, and ethnicity, while a physical examination form may list fields such as height, weight and systolic blood pressure. In another example, an adverse events form may identify (e.g. list) the fields for which data should be collected when a subject experiences an adverse event (e.g. fields such as adverse event type, a description of the adverse event, a severity of the adverse event may be identified).

A set of data collected using a particular form comprises values for each of the fields identified by that form. For example, a set data collected using a demographic comprises values (e.g. recorded for a particular subject, during a particular study event) for each of the fields that the demographics form comprises, such as age, gender, and ethnicity.

Different forms are used to record data taken during different study events. Each study event may identify one or more forms using which data are collected during that study event.

Form entry: As used herein, the term "form entry" refers to the set of data that is recorded for a particular subject, at a particular study event, using a particular form. A form entry collected using a particular form is referred to herein as belonging to that form. Similarly, a form entry collected for a particular study event is referred to herein as belonging to that study event. Similarly, a form entry collected for a particular subject is referred to herein as belonging to that subject. Finally, a form entry collected as part of a particular study is referred to herein as belonging to that study. Accordingly, data for a clinical trial comprises a series of form entries.

Item: As used herein, the term "item" refers to an individual clinical data item, such as the age of a single subject or a single systolic blood pressure reading.

Operational data: As used herein, the term "operational data" refers to data having to do with the process of creation, deletion, recordation, and/or modification of clinical data collected during a clinical trial. Non-limiting examples of operational data include audit records, queries, and signatures. For example, an audit record may comprise information such as who performed a particular action such as the creation, deletion, or modification of clinical data, as well as where, when, and why that action was performed. In another example, operational data comprises an electronic signature applied to a collection of clinical data. The electronic signature identifies a user that accepts legal responsibility for that data. The electronic signature may comprise an identification of the person signing, the location of signing, and the date and time of signing. In certain embodiments, the electronic signature comprises a meaning of the signature as defined via the U.S. Food and Drug Administration guidelines under 21 C.F.R. Part 11. The signature meaning may be included in an XML element, such as 'SignatureDef', in accordance with the Clinical Data Interchange Standards Consortium Operational Data Model specification. In certain embodiments, in the case of a digital signature, the signature comprises an encrypted hash of the included data.

By contrast, the data collected during a clinical trial such as observations by a medical practitioner of disease progression in a subject, demographic information about a subject, records of side effects, medical test results, and the like is referred to herein as "clinical data". The term "clinical trial data" includes both clinical data and operational data.

Table: As used herein, the term "table" refers to a grouping of related data. For example, a set of demographic data may be stored in a table, while a set of adverse event data may be stored in another table. A table may be represented in terms of rows and columns. Each column in the table may represent a different field, such as, for example, 'Date of Birth', or 'Gender'. As used herein, the term "name of a column," or "column name" refers to an identifier, such a string of text that labels a particular column. Typically the identifier is representative of the field that the particular column represents. For example, a column that represents the field 'Data of Birth' may have a column name of 'BRTHDTC'.

Each row in the table may represent a data set corresponding to a single record. For example, the record of the demographic information for each subject may be stored in a different row. In another example, such as the recording of adverse events, multiple records may exist for a single subject. Accordingly, the adverse events information for a subject may be stored in multiple rows, wherein each row corresponds to a record for that subject. The terms "rows" and "columns" are used to represent particular features of related data, and do not limit the manner of storage to a particular visual representation of a table, such as a spreadsheet with vertical columns and horizontal rows. For example, individual "rows" of a single table may be stored as separate documents in a data storage system, such as JSON.

Provide: As used herein, the term "provide", as in "providing data", refers to a process for passing data in between different software applications, modules, systems, and/or databases. In certain embodiments, providing data comprises the execution of instructions by a process to transfer data in between software applications, or in between different modules of the same software application. In certain embodiments a software application may provide data to another application in the form of a file. In certain embodiments an application may provide data to another application on the same processor. In certain embodiments standard protocols may be used to provide data to applications on different resources. In certain embodiments a module in a software application may provide data to another module by passing arguments to that module.

DETAILED DESCRIPTION OF THE INVENTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

The systems and methods described herein relate to a merge technology that enables merging of clinical trial data from different sources. Examples of sources of clinical trial data include clinical trial data collected using different forms (e.g. eCRFs collected via an EDC system) from the same study, or different forms from different studies.

FIG. 1 is a block flow diagram showing the organization of components and subsystems associated with a merge system architecture, according to an illustrative embodiment. As shown in FIG. 1, the architecture 100 comprises a data table import module 132, a table merge/unmerge module 134, a column mapping/unmapping module 138, and a data type conversion module 139 (collectively 130). The system takes as input clinical trial data from one or more datasets 112, 114, 116, 122, 124, 126 of one or more studies (collectively 110 and 120), and outputs a custom merged table 140.

Clinical trial data is input to the system via the data table import module 132, which obtains the data belonging to one or more forms (e.g. data collected using one or more different eCRFs) and represents such data in a tabular format, as a source table. Each form is used to record a different type of data for a given study event. When the data from one or more forms are represented as a data table, the records for each different subject typically correspond to different rows in the data table. Each column in the data table typically corresponds to a field of the form. Accordingly, each cell represents the value recorded for a particular field corresponding to a particular subject. In certain cases, such as the recording of adverse events data, there may exist multiple records for a single subject, and, accordingly, one or more rows for each subject. In addition, a source table may comprise operational data (e.g. an audit record, a query, a comment, an electronic signature), in which each attribute (e.g. a field, such as an identifier of a user associated with the audit record, query, comment, or electronic signature, e.g. a field such as a date of the audit record, query, comment, or electronic signature) corresponds to a different column in the source table that stores the value associated with the field (e.g. the value of the user identifier, the value of the date).

In certain embodiments, the methods and systems described herein may obtain tabular data that has been created from source data retrieved from an EDC source, using the methods and systems described in U.S. patent application Ser. No. 15/233,847 "Caching Technology for Clinical Data Sources", the entire contents of which is hereby incorporated herein by reference.

Figure 2:
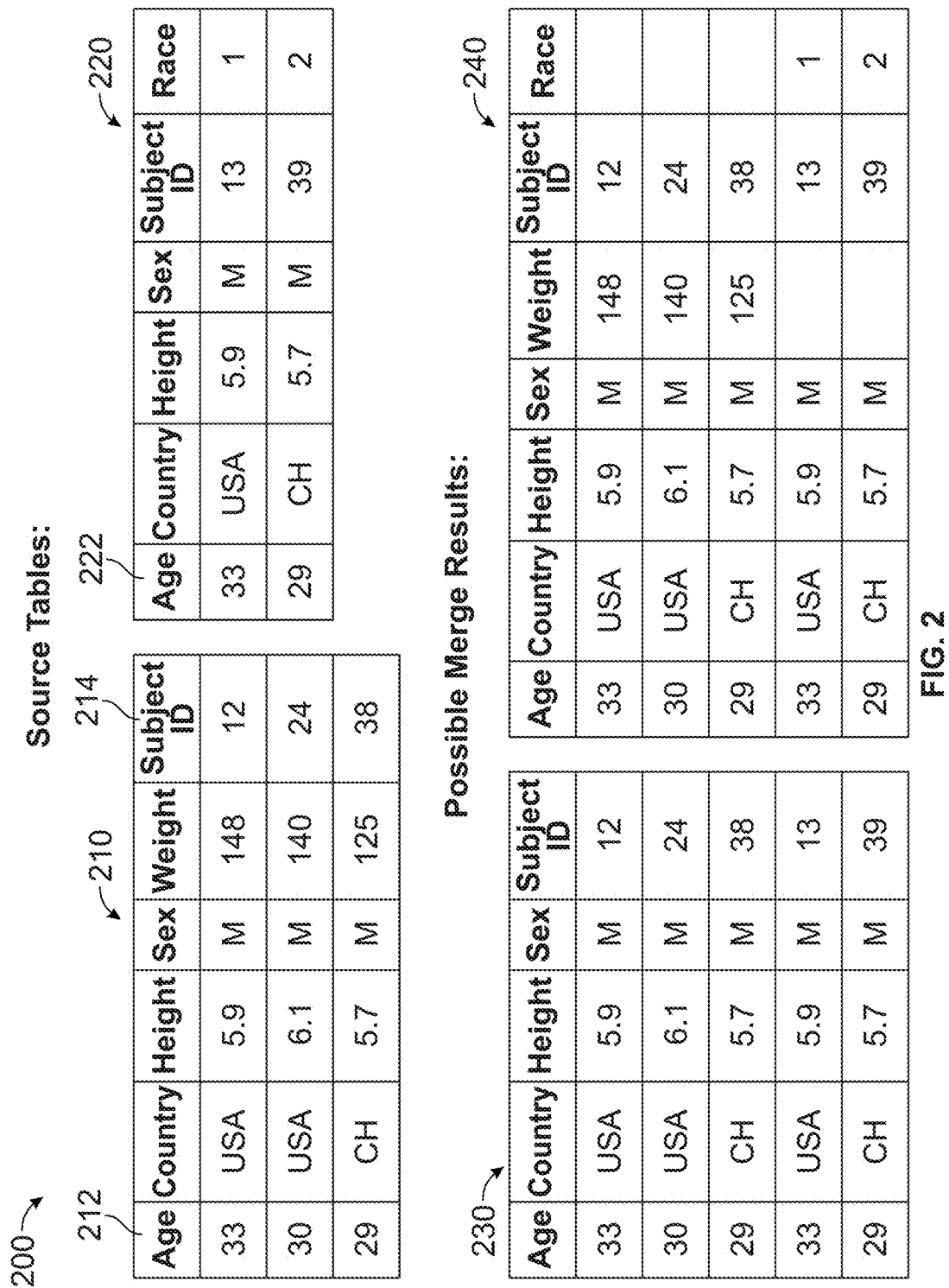
FIG. 2 is schematic of a process for merging two source tables to produce to possible resultant merged tables, according to an illustrative embodiment.

In certain embodiments, the table merge/unmerge module 134 provides the functionality to merge two or more source tables, in order to generate a single merged table 140. FIG. 2 provides an illustrative embodiment of the process 200 of merging two source tables. A first source table 210 stores data that was collected in a first study event, such as an event in which demographics information was recorded for a set of subjects in the clinical trial. The first source table 210 comprises a series of columns, each of which represents a different field, and each of which has a different column name. For example, a first column named 'AGE' 212 represents a subject age field. In the example of FIG. 2, the first source table comprises three rows. In general, a first source table comprises an arbitrary number, n, of rows (e.g. the first source table comprises n rows, wherein in the example of FIG. 2, n=3). Each of the values stored in a different row of the column corresponds to a recorded value of the age of a different subject. Similarly, a second column 214, named 'SUBJECTID' represents a field corresponding to an identifier (e.g. a number in the example of FIG. 2) that uniquely labels each subject a subject id. Each of the subject-ids for the different subjects are stored in a different row of the column.

Similarly, a second source table 220 stores data recorded during a second study event, such as a follow-up to the first study event in which a second set of demographics data was recorded for another set of subjects. The second source table 220 comprises a series of columns, each of which represents a different field, and each of which has a column name. As with the first source table, each of the values stored in a different row of the column corresponds to a value recorded from a different subject. In the example of FIG. 2, the second source table comprises two rows. In general, a second source may comprise an arbitrary number of m rows (e.g. the second source table comprises m rows, wherein in the example of FIG. 2, m=2).

In certain embodiment, a first step in the process of merging the first and second source tables to create a single merged table comprises determining which of the columns in the second source table represent the same (e.g. or an equivalent) field as a respective column in the first table. For example, the first source table includes columns having names 'AGE', 'COUNTRY', 'HEIGHT', 'SEX', 'WEIGHT', and 'SUBJECTID' that represent fields such as a subject age, country of origin, height, sex (e.g. gender), weight, and subject-id respectively. The second source table comprises columns having names 'AGE', 'COUNTRY', 'HEIGHT', 'SEX', 'SUBJECTID', and 'RACE' that represent fields such as a subject age, country of origin, height, sex (e.g. gender), subject-id, and the race of the subject respectively.

Accordingly, the methods and systems described herein may automatically determine that certain columns in the second source table represent the same fields as certain columns in the first source table. For example, the column named 'AGE' in the second source table 222 represents the same field (e.g. a subject age) as the column named 'AGE' in the first table 212. In certain embodiments, the systems and methods described herein determine that a column in the second source table represents the same field as a column in the first source table by matching the names of the columns, such that each column in the second table that has a column name that is the same as the name of a respective column in the first source table is determined to represent the same field as the respective column in the first source table.

Once two columns are determined to represent the same field, they may be "mapped" to each other. As used herein, the term "mapped", as in a first column is mapped to a second column, refers to the identification that the first and second columns represent the same field (e.g. they are labelled as columns that represent the same field). For example, a software routine may store a list of the names of the columns in the first source table, and for each column in the first source table, a respective (if any) name of column in the second source table that is mapped to the column in the first source table. The mapping of one column to another column can be identified, documented, recorded, and/or stored in other ways as well.

Similarly, the terms "map" and "mapping", as in the system may map a first column to a second column, as used herein refer to the act of making the identification that a first and second column represent the same field, which may include the determination that they represent the same field. The reverse process—"unmapping"—is the removal of the identification that two columns represent the same field.

Accordingly, turning again to FIG. 2, the methods and systems described herein may map the 'AGE', 'COUNTRY', 'HEIGHT', 'SEX', and 'SUBJECTID' columns of the second source table 220 to the respective 'AGE', 'COUNTRY', 'HEIGHT', 'SEX', and 'SUBJECTID' columns of the first source table 210.

In certain embodiments, once the common columns (e.g. the columns that represent the same fields) in the first and second source tables are mapped to each other, the methods and systems described herein produce a merged table 230 that combines the data values stored in the mapped columns of the first and second source tables. Each of the columns in the resultant merged table 230 corresponds to a column in the first source table that is mapped to a column in the second source table. For each mapped column, the n values stored in the column of the first source table are stored in the first n rows (e.g. in consecutive rows 1 through n) of the corresponding column of the merged table. Them values stored in the column of the second source table that is mapped to the column of the first source table are stored in consecutive rows n+1 through n+m, immediately following rows 1 through n of the corresponding column in the merged table. In certain embodiments, the merged table 230 comprises only the values from columns from the first source table to which a column in the second source table is mapped and only the values from the columns in the second source table that are mapped to a column in the first source table.

In certain embodiments, the merged table also comprises values from the columns of the first source table to which no column in the second source table is mapped, and values from the columns of the second source table that are not mapped to any column in the first source table. Accordingly, a resultant merged table such as merged table 240 may be generated. In the merged table 240 the n values from each column of the first source table to which no column of the second source table is mapped are stored in consecutive rows 1 through n of a corresponding column in the merged table, leaving immediately following consecutive rows (n+1) through (n+m) blank. Similarly, the m values from each column of the second source table that is not mapped to a column in the first source table are stored in consecutive rows (n+1) through (n+m) of a corresponding column of the merged table immediately following rows 1 through n, leaving rows 1 through n blank.

The merge process described herein can be extended to more than two source tables. Accordingly, an arbitrary number of source tables can be merged to produce a single custom merged table.

In certain embodiments, no two rows in either of the first source table and the second source table will be identical. In particular, the combination of values that are stored along each row in the first source table and the second source table will be distinct from the combination of values that are stored along any other row in either the first or second source table.

For example, a particular source table (e.g. either the first source table or the second source table) may comprise a column representing a subject-id (e.g. SubjectID), which is a unique identifier of each subject participating in the study to which the clinical trial data stored in the particular source table belongs. Accordingly, in certain embodiments, the subject-id value will be different for each row in the source table such that no two rows in a particular source table are the same. In certain embodiments, wherein the particular source table comprises multiple records for a single subject, such as in the case of a source table comprising adverse events data, other values stored in each row will serve to differentiate each row in the particular source table from all the other rows in the source table.

Similarly, a first source table may also comprise a column whose values serve to differentiate a row in the first source table from any row in a second source table. For example, if a first and second source table comprise data from different study events within the same study, each of the first and second source table may comprise a column that represents a unique identifier of a study event—a study event-id (e.g. 'StudyEventOID'). Accordingly, each row in the first source table will comprise a study event-id that is distinct from the study event-id of any of the rows in the second source table. Therefore, every row in the first source table will be distinct not only from any other row in the first source table, but also distinct from any row of the second source table.

Likewise, if the first and second source tables are from different studies, each of the first and second source tables may comprise a column representing a unique identifier of the particular study to which the each table belongs—a study-id (e.g. 'StudyOID'). As with the study event-id, the study-id column will differentiate a given row in the first source table from the rows in the second source table.

In certain embodiments, the column mapping/unmapping module 138 provides the functionality to map one or more columns in the one or more source tables to columns in another source table. The column mapping/unmapping module 138 also provides the functionality to unmap one or more columns from a particular source table from a column in another source table to which it was previously mapped.

Finally, in certain embodiments, the data type conversion module 139 provides the functionality to change the data types for one or more columns in either a newly created merged table or an existing data table. The final output of the merge process implemented by the merge systems described herein is a custom merged table 140 that contains the specific subsets of data from multiple forms from one or more clinical trial studies.

In certain embodiments, the merge process can be controlled by user interaction with an intuitive GUI that frees the user from the need to learn complex programming languages and write code to process their data.

Figure 3A:
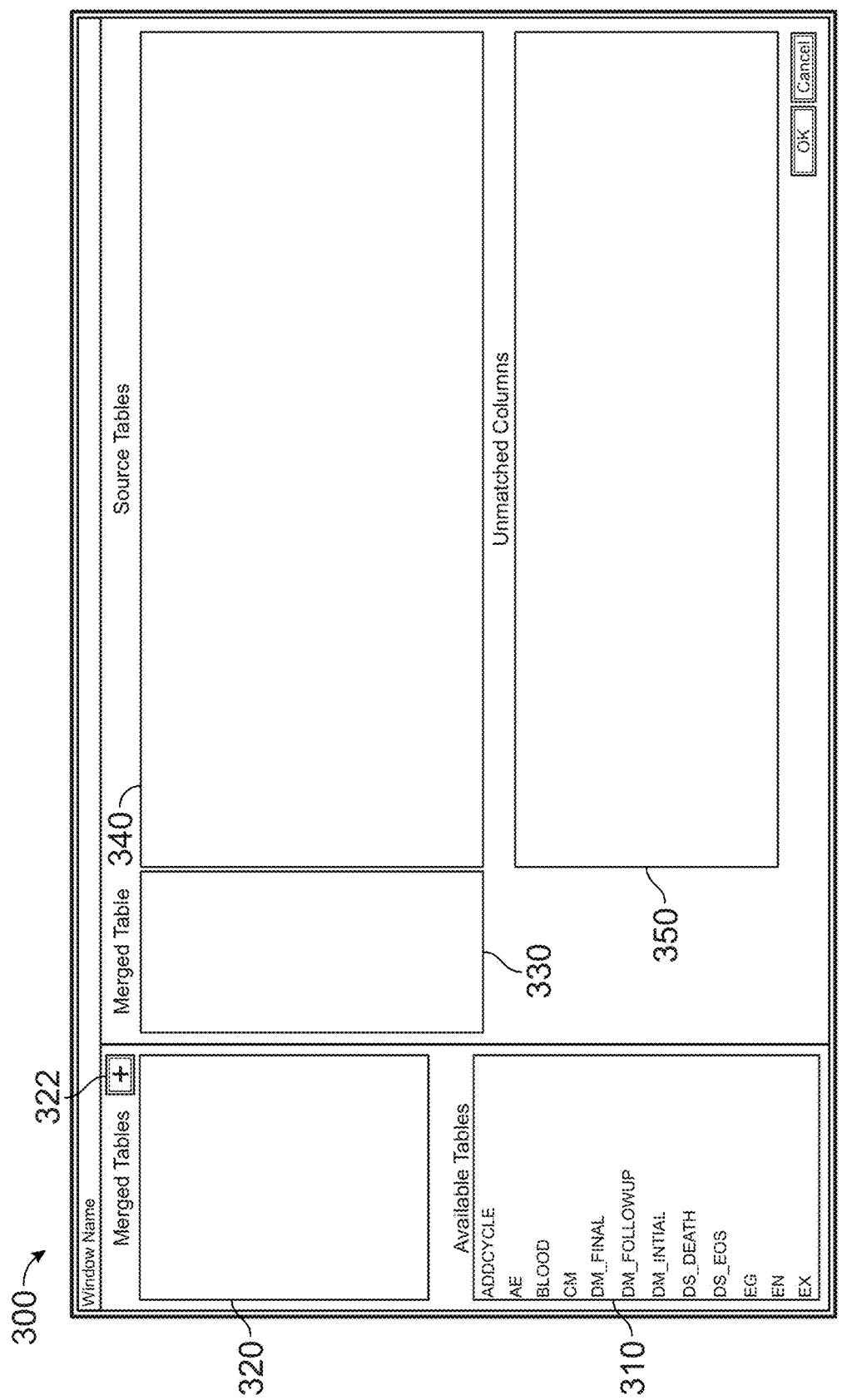
FIG. 3A is a screenshot of a graphical user interface implementing the merge technology, according to an illustrative embodiment.

FIG. 3A shows a screenshot of an example of a user interface 300 for a system implementing the merge technology according to an illustrative embodiment. The screenshot shows different panes in the main window of the data merging user interface. The available tables pane 310 displays a list of the data tables that have been imported from a clinical study. In certain embodiments, data tables from a single clinical study are imported and displayed in the pane.

In certain embodiments, data tables from one or more different clinical studies may be imported and displayed in the pane.

The merged tables pane 320 displays the options to create new tables by merging two or more data tables selected from the list of available data tables. In the example step shown in the screenshot shown in FIG. 3A, no merged tables have been created, and, accordingly, the list of custom merged tables displayed in the merged tables pane 320 is empty. A user may create a new merged table by, for example, clicking the plus button 322 adjacent to the merged table pane 320.

Once a merged table is created, it may be assigned a name, and the name is listed in the merged tables pane. Similarly, the source tables pane 330 and unmatched columns pane 340 are both initially empty (e.g. as shown in FIG. 3A).

Figure 3B:
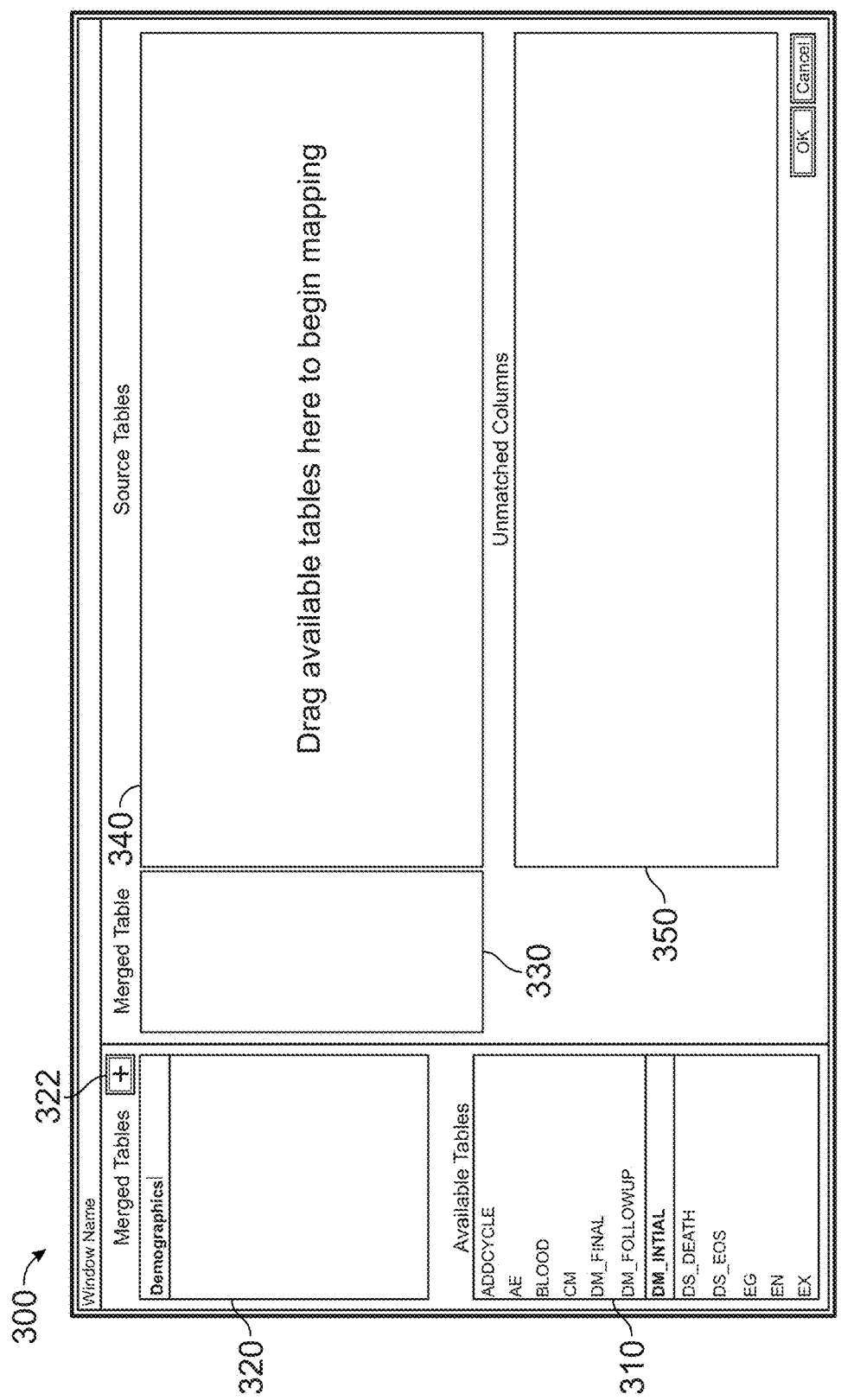
FIG. 3B is a screenshot of a graphical user interface implementing the merge technology that shows a user input corresponding to the creation and entering of a name for a new merged table to be created, according to an illustrative embodiment.

In certain embodiments, after importing clinical data from one or more clinical trials, a user generates a new custom data table by merging two or more available source tables. In certain embodiments, a first step in the merge process for creating the custom merged table is the creation of a new data table. As shown in the screenshot of FIG. 3B, a user may click the plus sign 322 to create the new data table, and input a name for the new data table (e.g. Demographics).

Figure 3C:
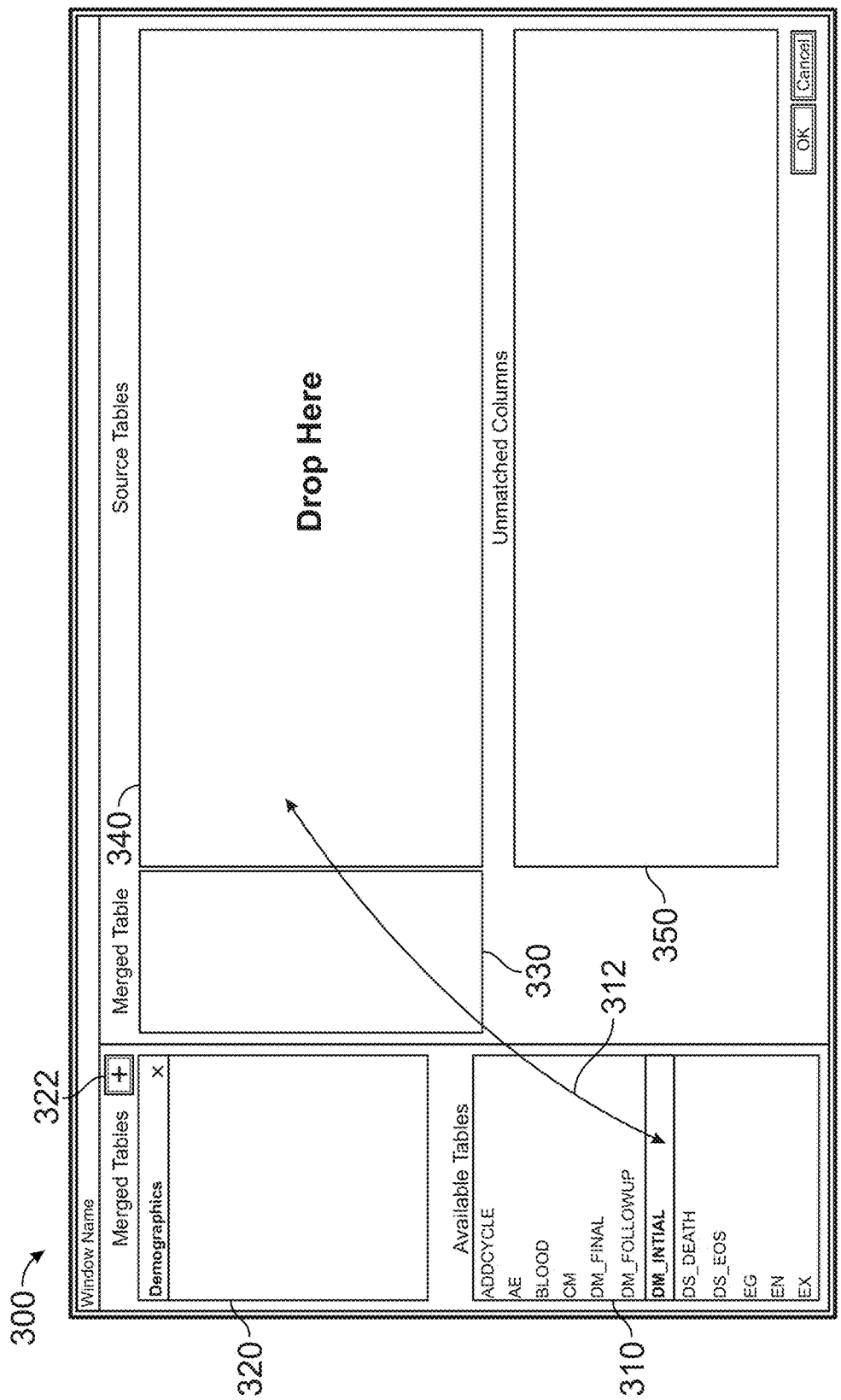
FIG. 3C is a screenshot of a user interaction with a user interface implementing the merge technology that shows a user input corresponding to the selection of a first source table, according to an illustrative embodiment.

In a next step in the merge process, two or more source tables are selected. In FIG. 3C, a first source table (e.g. labelled 'DM_INITIAL') is specified by dragging the text corresponding to the name of the first source table from the list of available tables, and then dropping the text into the window area corresponding to the source tables pane in the user interface (312). The first source table stores the subject data from a particular form (e.g. data collected using a particular eCRF).

Figure 4:
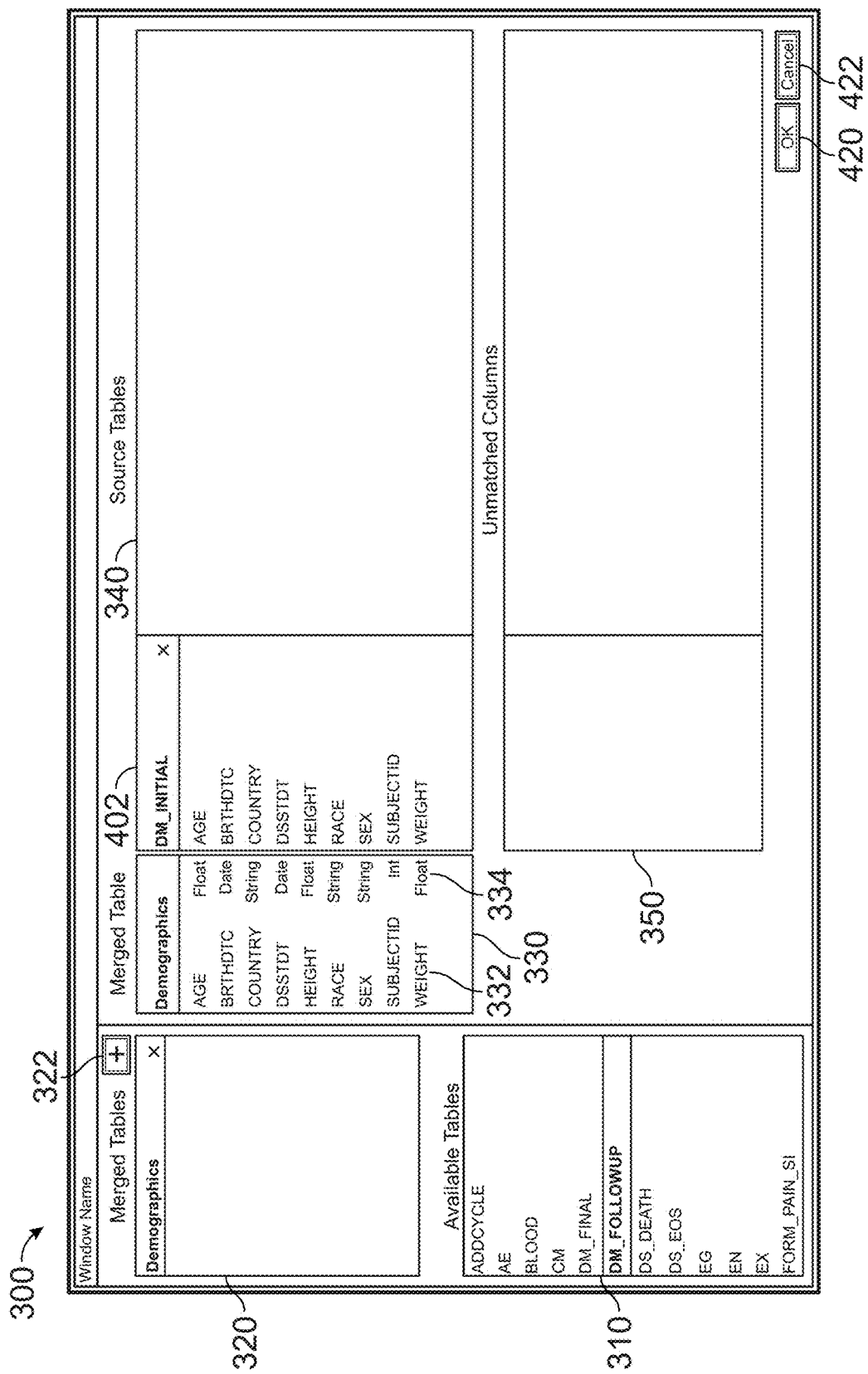
FIG. 4 is screenshot of a user interface displaying the name of a first source table along with the names of each of the columns of the first source table as well as the names of each of the columns to be included in the final merged table, along with the corresponding data types, according to an illustrative embodiment.

Turning to FIG. 4, following the selection of the first source table, the column names of the first source table are identified, and these column names are displayed in the source table pane under the 'DM_INITIAL' data table heading 402. Additionally, columns are created in the newly generated custom merged table corresponding to the identified columns of the first source table. The names of the columns 332 to be included in custom merged table are listed in the merged table pane 330. Additionally, the data type 334 of each column to be included in the merged table that will be used to store the values is identified and displayed to the right of the column names in the merged table pane. In certain embodiments, the data types that will be used to store the values for each column in the merged table are initially determined to be the data types that are used to store the values in the corresponding column of the first source table. In certain embodiments, as will be described herein, the data type that is used to store the values of a particular column in the merged table may be changed to a new data type that is different from the original data type.

Figure 5:
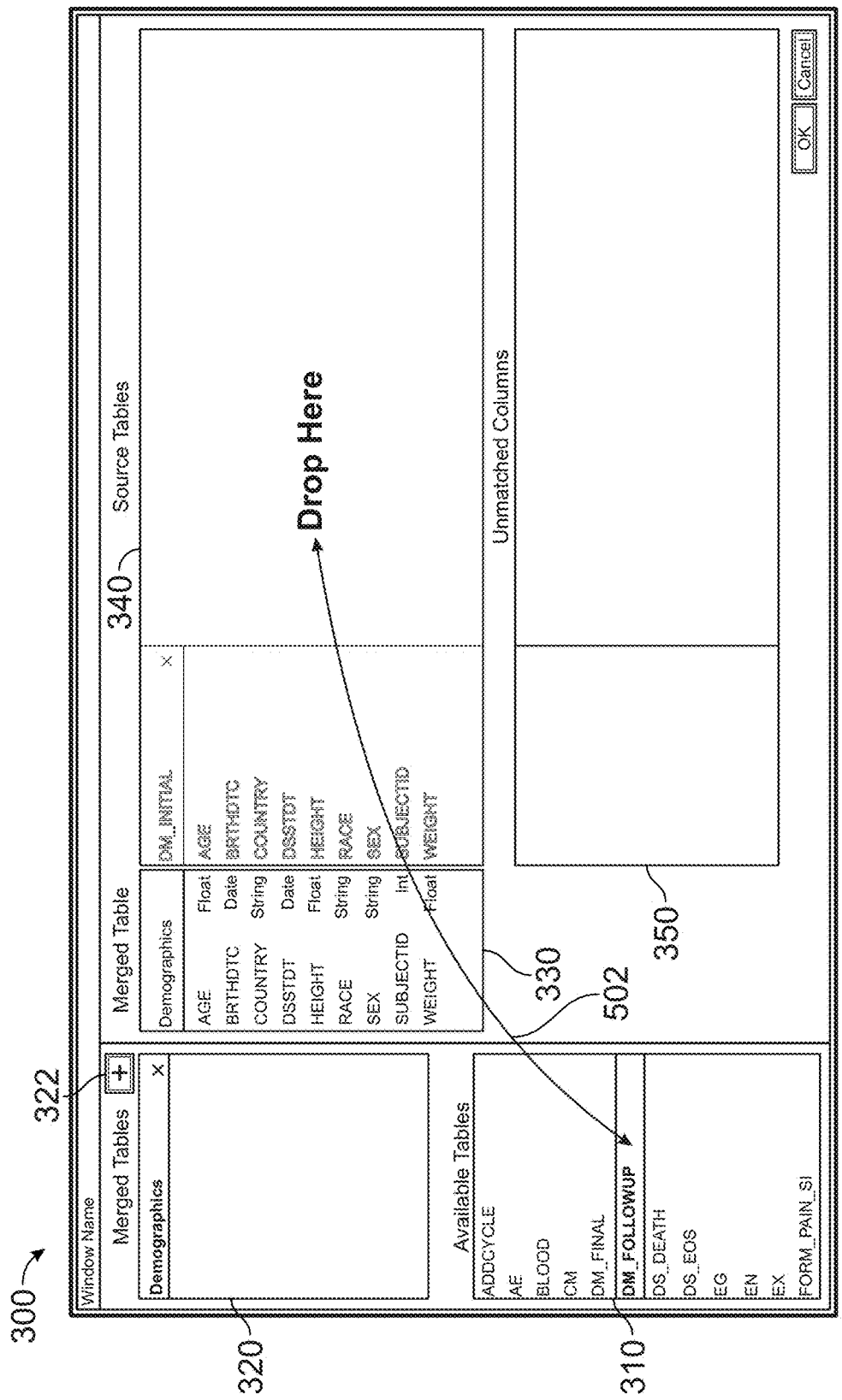
FIG. 5 is a screenshot of a user interaction with a user interface implementing the merge technology that shows a user input corresponding to the selection of a second source table, according to an illustrative embodiment.

Turning to FIG. 5, in a next step in the illustrative embodiment a user selects a second source table via the drag-and-drop process (502). This second source table will be merged with the first source table to generate the new merged table. Typically, the second source table will store data that is similar or related, but not necessarily identical, to the data stored in the first source table. For example, some of the names of the columns in the second source table may overlap with (e.g. the names may match) the names of the columns in the first source table. In certain embodiments, columns in the second source table that have a name matching a name of a column in the first source table are automatically mapped to the matching column of the first source table.

Figure 6:
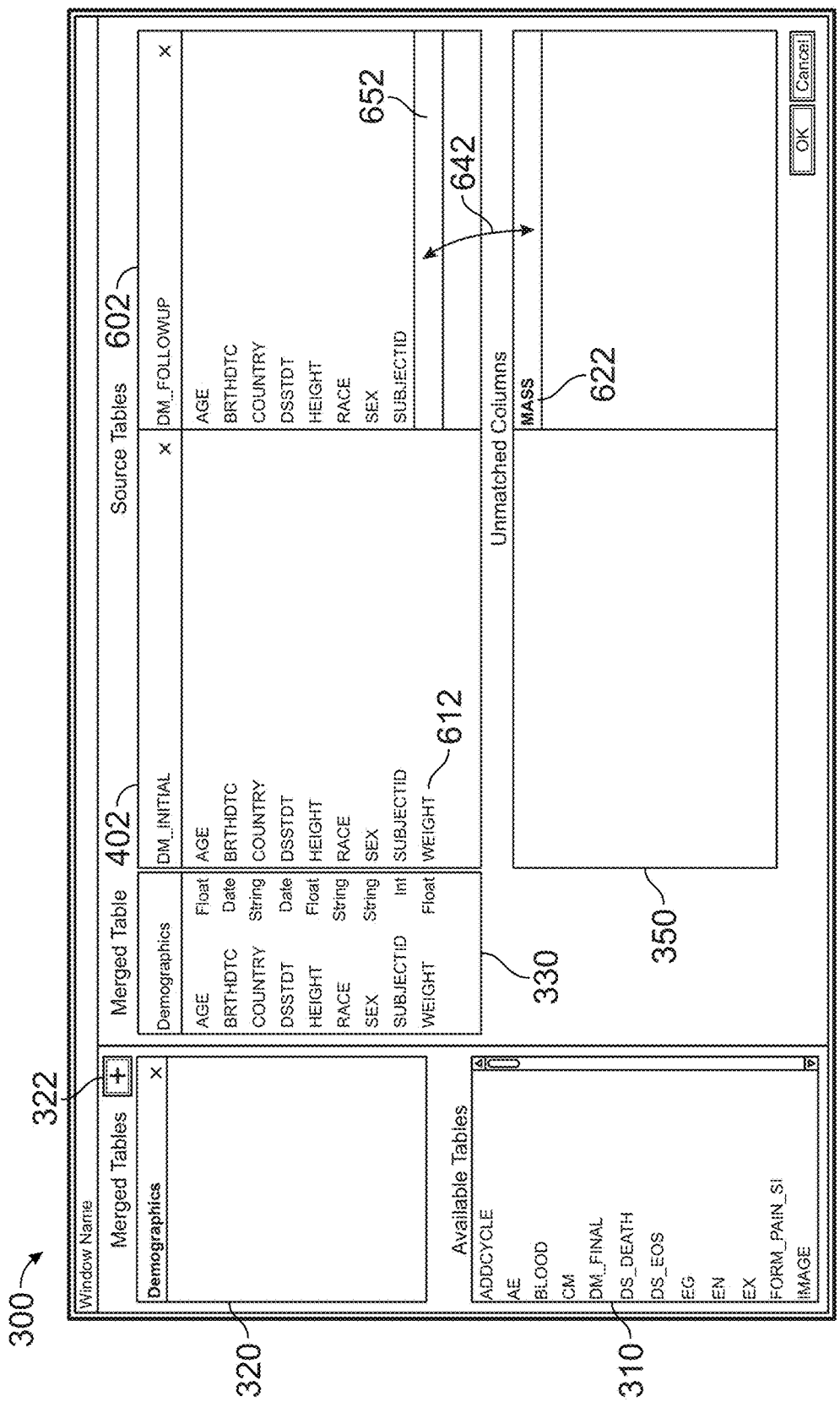
FIG. 6 is a screenshot of a user interaction with a user interface implementing the merge technology that shows a user input corresponding to the selection of a column in the second source table in order to map the selected column of the second source table to a selected column of the first source table, according to an illustrative embodiment.

Additionally, certain columns that are present in the first source table may be absent from the second source table. Likewise, certain columns that are present in the second source table may be absent from the first source table. FIG. 6 shows an example of the second source table 602 to be merged with the first source table 402. A portion of the columns in the second source table also exist in the first source table. The 'WEIGHT' column 612, however, is found in the first source table, but not in the second source table. The 'MASS' column 622 is found in the second source table but not the first source table. Any unmapped columns from the second source table are initially displayed in the unmatched columns pane 350 of the GUI.

Figure 7A:
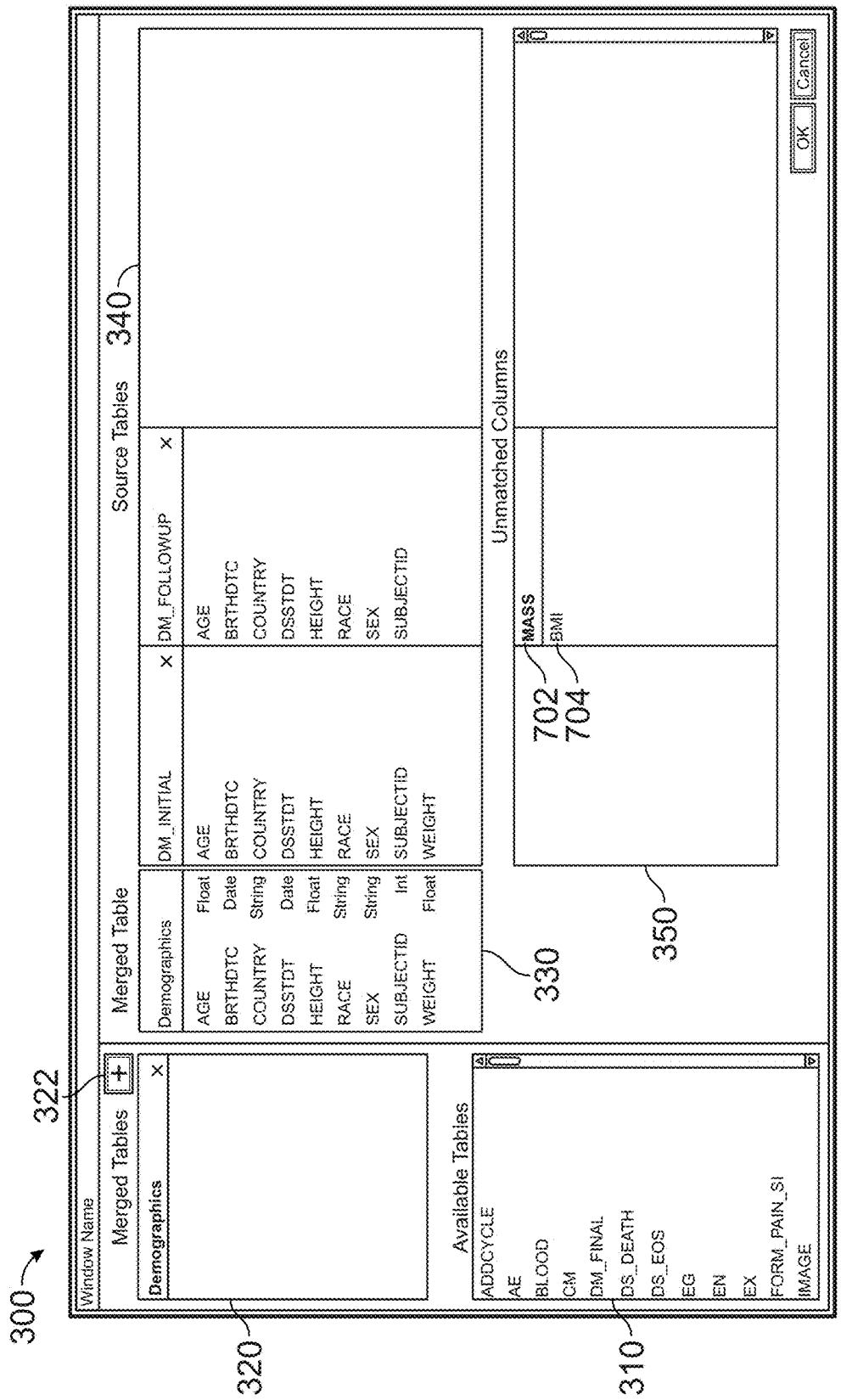
FIG. 7A is a screenshot of a user interaction with a user interface implementing the merge technology showing a second source table that comprises two columns that are not mapped to any of the columns of the first source table, according to an illustrative embodiment.
Figure 7B:
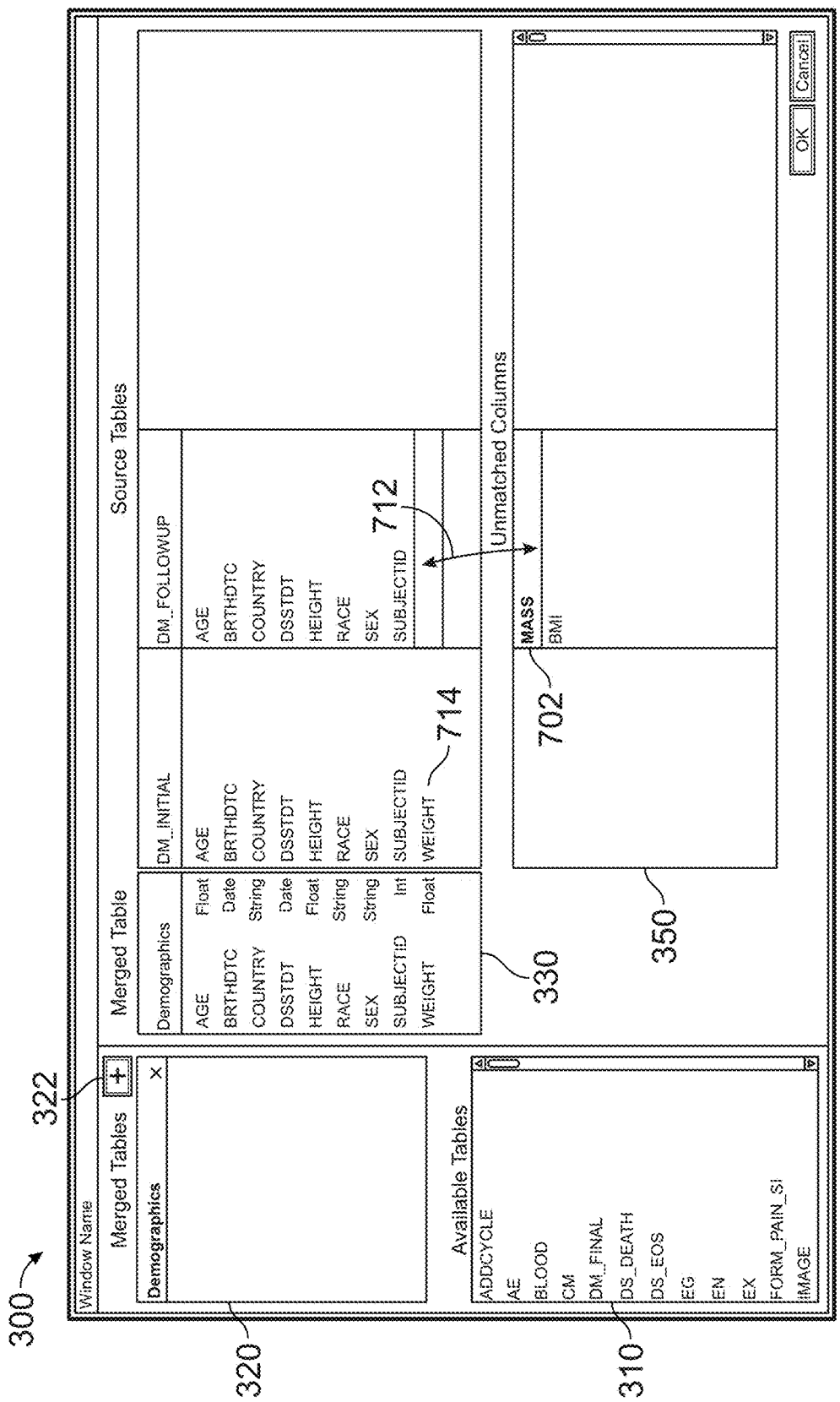
FIG. 7B is a screenshot of a user interaction with a user interface implementing the merge technology that shows a user input corresponding to the selection of a column in the second source table in order to map the selected column of the second source table to a selected column of the first source table, according to an illustrative embodiment.
Figure 7C:
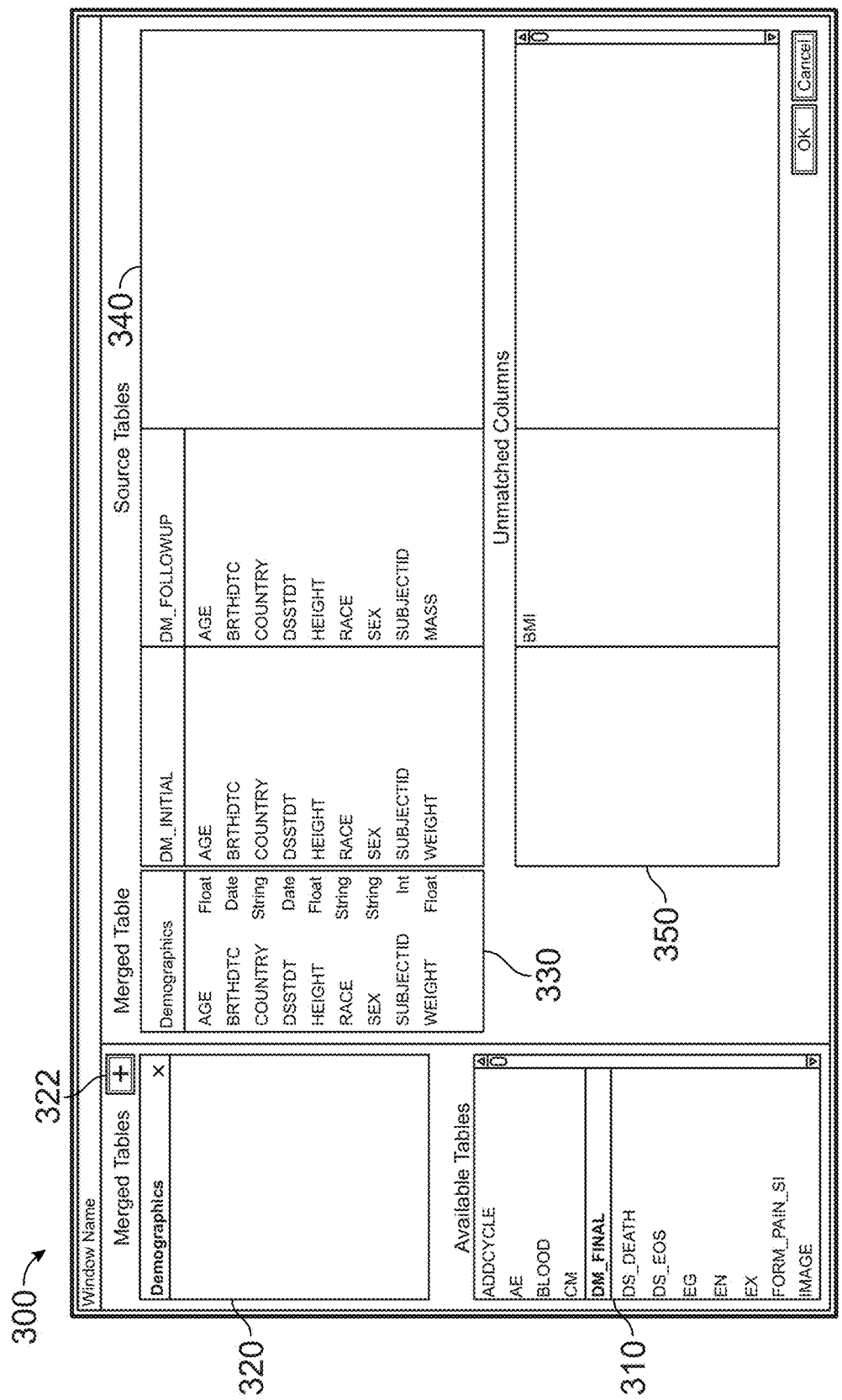
FIG. 7C is a screenshot of a user interface implementing the merge technology showing the result of a user input to map a column from a second source table to a column of a first source table, according to an illustrative embodiment.

In certain embodiments, two or more columns from different source tables which are identified with different column names (e.g. and thus, not automatically mapped to each other), but represent similar data (e.g., the first source table contains a column labeled 'WEIGHT' 612, while the second source table contains a column labeled 'MASS' 622) can be mapped to each other via user interaction in the GUI. In particular, after selecting a source table, a user may provide an input via the interface to map any of the columns from the selected source table to any column from another source table. Continuing with the example of FIG. 6, the user can provide an input to map the 'MASS' column 622 from the second source table to the 'WEIGHT' column 612 from the first source table by dragging the text corresponding to 'MASS' from the unmatched columns pane 350 and dropping it in the source tables pane in the row 642 adjacent to the 'WEIGHT' entry (652). Accordingly, the generated merged table will contain a single column with values from the 'WEIGHT' column of the first source table 612 and the 'MASS' column 622 of the second source table. Similarly, turning to FIG. 7A, a second source table may comprise two columns that do not match any of the columns in the first source table. In FIG. 7A, the 'MASS' 702, and 'BMI' 704 columns are, accordingly, not automatically mapped to a column in the first source table. The user may use the GUI to select the 'MASS' column 702 to be mapped to the 'WEIGHT' column 714 of the first source table as shown in FIG. 7B (712), but choose not to map the 'BMI' column to any of the columns in the first source table (FIG. 7C). Accordingly, in certain embodiments, the merged table resulting from the process of merging the first and second source tables may comprise only the values of the columns from the first and second source tables that are mapped to each other (e.g. only the columns displayed in the source tables pane).

Figure 8A:
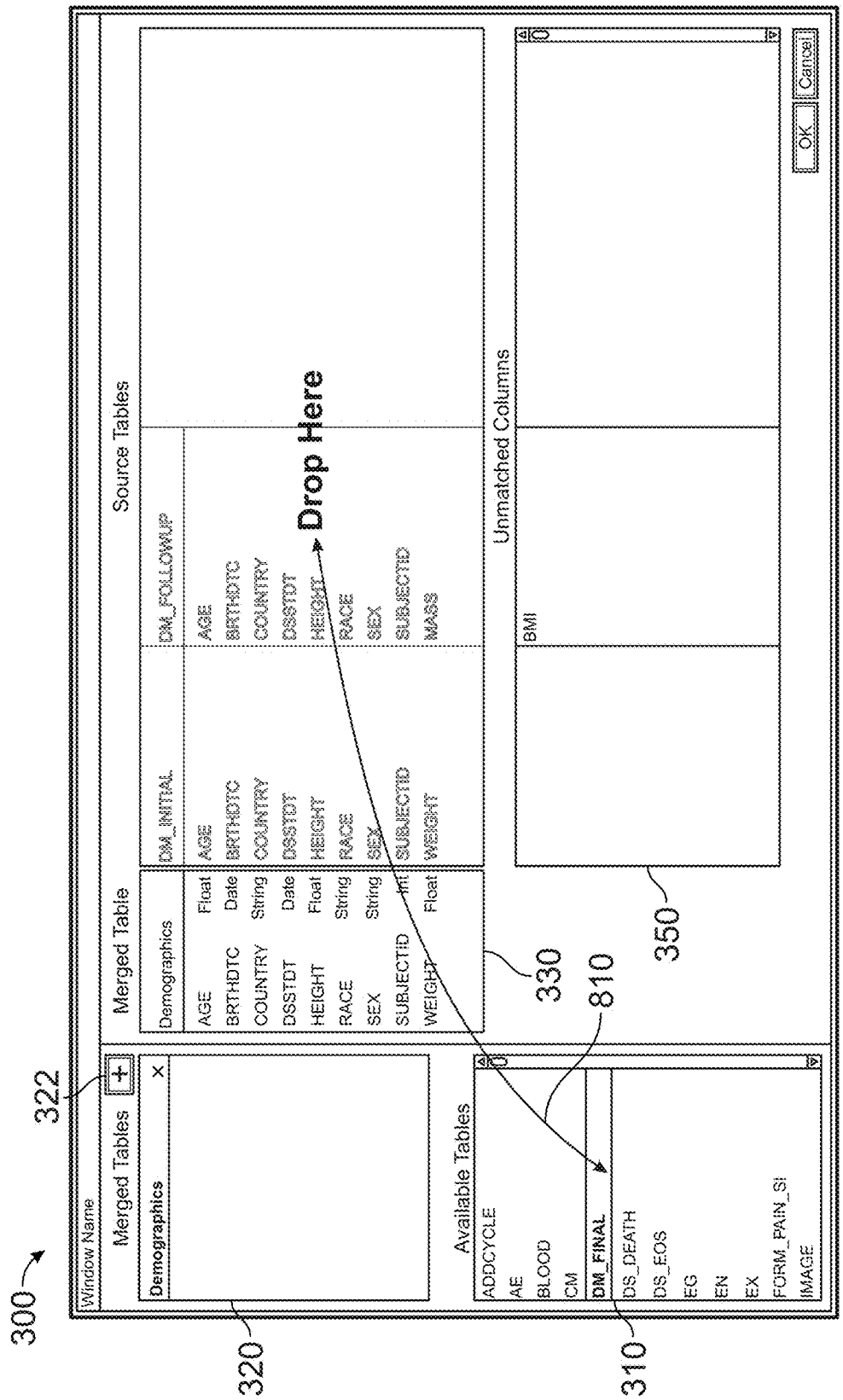
FIG. 8A is a screenshot of a user interaction with a user interface implementing the merge technology showing a user input corresponding to the selection of an additional source table to merge with a first and second source table, according to an illustrative embodiment.
Figure 8B:
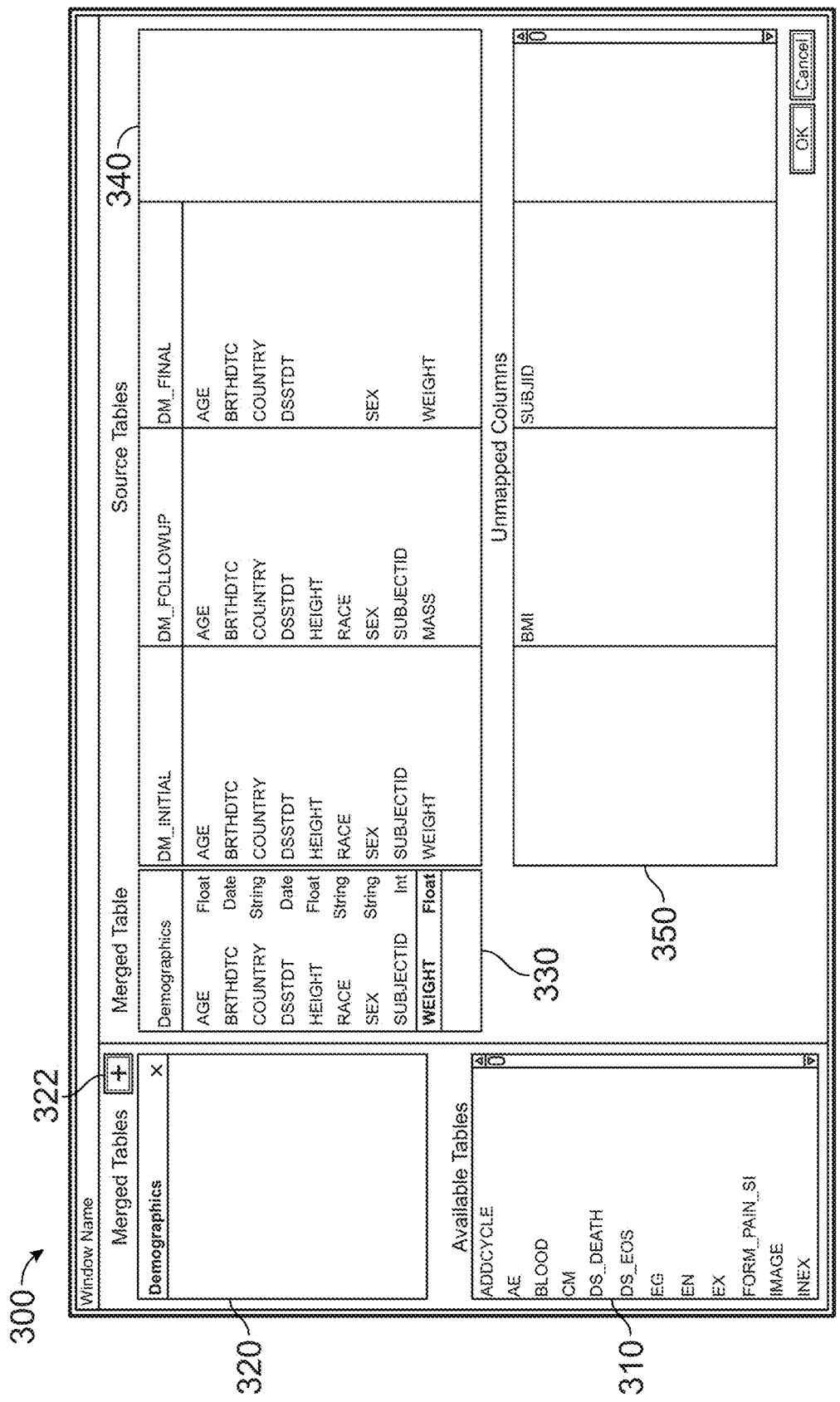
FIG. 8B a screenshot of a user interface implementing the merge technology that shows the result of a user selection of an additional source table to be merged with a first and second source table, according to an illustrative embodiment.

In certain embodiments, additional source tables may be selected as desired by the end user using a drag-and-drop process (810), as illustrated in FIG. 8A. The additional source tables will be merged with the previously selected source tables to generate the new merged table. In an embodiment, columns in the additional source tables that have a name matching a name of a column in any previously selected source table are automatically mapped to the matching column of the previously selected source tables. Columns in the additional source tables that have names that do not match a name of a column in any previously selected source tables will remain unmapped, as illustrated in FIG. 8B.

Figure 8C:
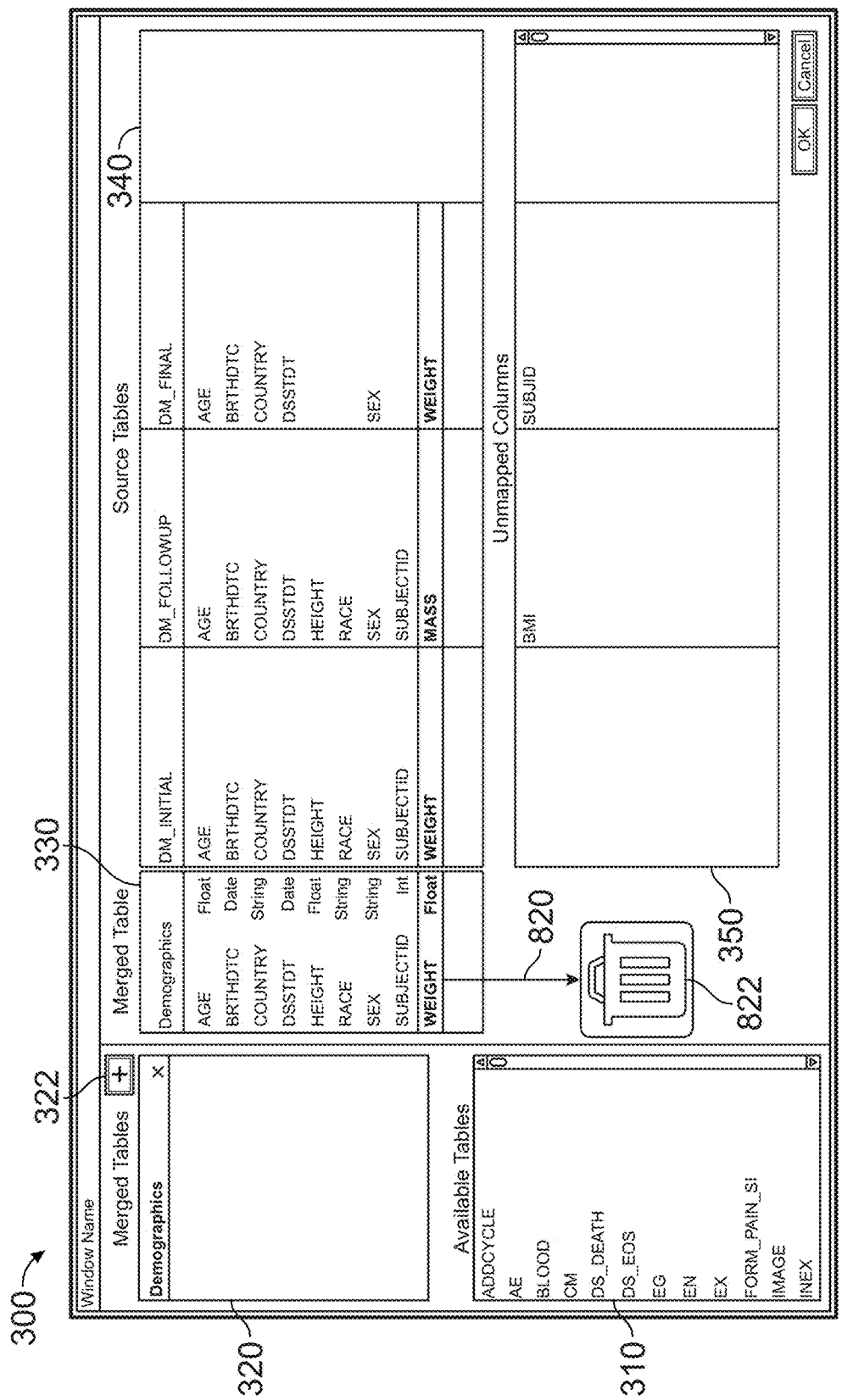
FIG. 8C is a screenshot of a user interaction with a user interface implementing the merge technology that shows a user input corresponding to the selection of a column in the merged table to be removed, according to an illustrative embodiment.
Figure 8D:
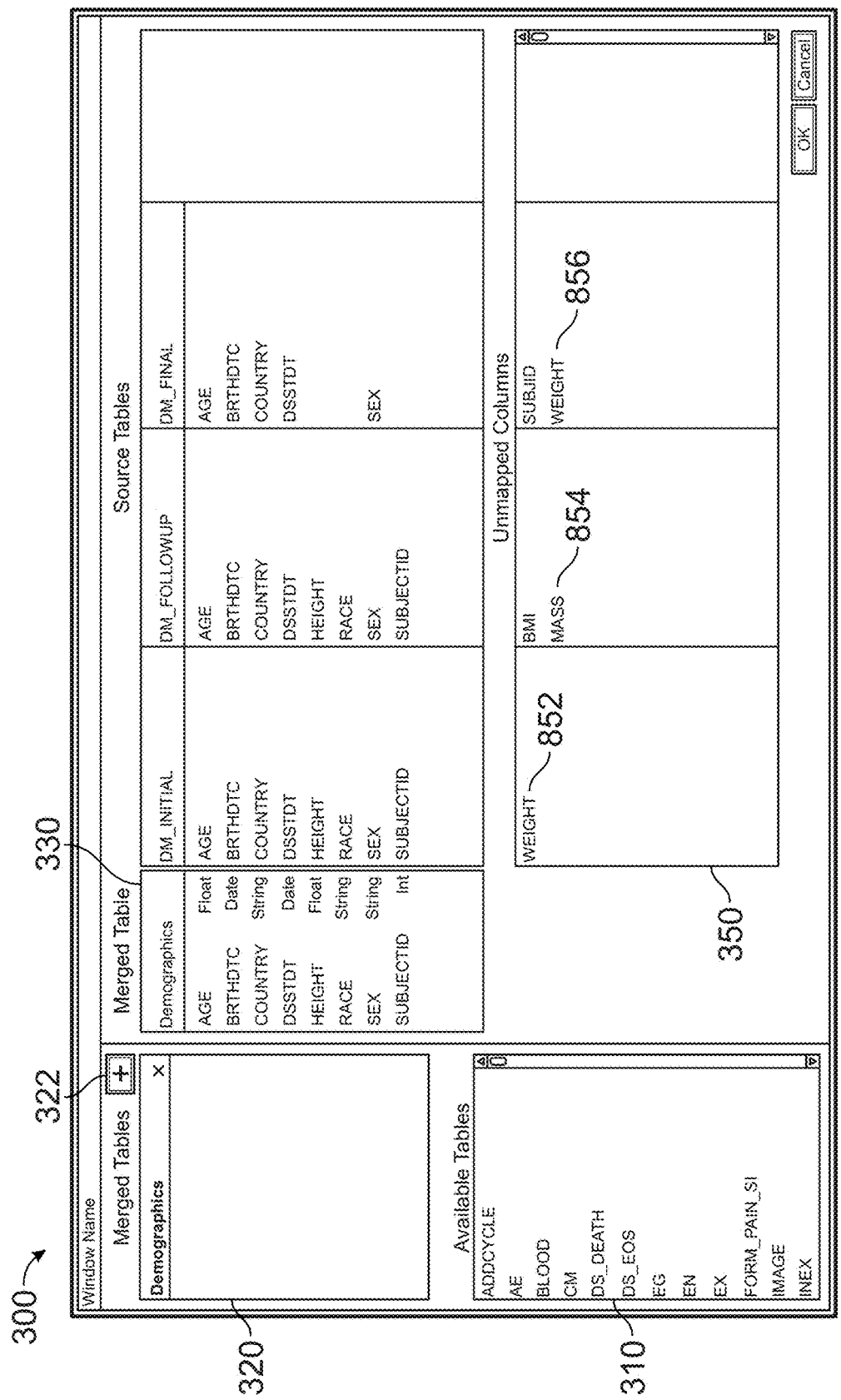
FIG. 8D is screenshot of a user interface implementing the merge technology that shows the result of a user input corresponding to the removal of a column from the merged table, according to an illustrative embodiment.

In certain embodiments, the user may precisely specify whether a column of a source table is to be included in the merged table, regardless of whether or not the column has been mapped to any other column of any other source table. For example, referring to FIG. 8C, the user may drag the entry corresponding to 'WEIGHT' from the merged table pane 330 and drop the entry into the icon of the trashcan 822 in order to remove the 'WEIGHT' column from the merged table (820). The 'WEIGHT' column is removed from the merged table, and any column from any source table mapped to the 'WEIGHT' column (e.g. the 'WEIGHT' column of the first source table 852, the 'MASS' column of the second source table 854, and the 'WEIGHT' column of the additional, third source table 856) is unmapped and shown in the unmatched columns pane 350, as shown in FIG. 8D.

In certain embodiments, after all the data tables have been imported, and their columns are mapped/unmapped to each other, a final data type conversion step may be performed for one or more columns in the final custom merged table. For example, the data types 334 associated with each column in the final custom merged table may initially be determined from the data types associated with the columns of the first source table that was imported, as shown in FIG. 4. Depending on the particular data to be stored in a given column (e.g. subject-id, age, birthdate, sex, weight) one or more respective data types may be appropriate. For example, if the subject-id is a list of numbers (e.g. '12', '12348', etc.) it may be most appropriately stored as an integer data type, or a string data type. The sex of a subject may be stored as a string (e.g., 'Male', 'Female', 'M', 'F') or an integer (e.g., '0' representing male, '1' representing female). The weight of a subject may be best represented as a floating point number.

Depending on the nature of the data, and how it will be used (e.g. how it will be used depends on the particular application of a given stakeholder) it may be preferable to store the data as one data type versus another. For example, storing subject-id data via an integer data type may be advantageous in certain cases (e.g. if mathematical operations such as addition, subtraction, greater than/less than comparison are to be performed on the data), while storing subject-id data as a string data type may be desirable in other cases (e.g. indexing particular digits is often built in to string methods).

Accordingly, in certain embodiments, the merge technology described herein enables a user to change the data type for storing data in different columns via the user interface shown in FIG. 4. For example, a user may edit the data types 334 (e.g. by entering new text, clicking and selecting from a drop down menu) displayed next to each column in the merged table pane that shows the columns and data types of the final custom merged table. In certain embodiments, once the user completes selection of a new data type, the data stored in the associated column is converted to the new data type.

Once the user is satisfied with the columns, column mapping, and column data types they have defined via the user interface, the user can confirm the completion of the merge process and creation of their custom merged table. For example, a user may click the OK button 420 to confirm the completion of the merge process. After the OK button 420 is clicked, the newly created custom merged table may be added to the list of available data tables.

In certain embodiments, if the user is dissatisfied with the merge process at any point, the cancel button 422 may be used to step-out of the merging process at any stage.

In certain embodiments, once a custom merged table has been created, the values of the custom merged table may be automatically updated as new clinical trial data is collected and retrieved from sources of clinical trial data. Accordingly, once a user (e.g. a stakeholder) has created a custom merged table that comprises the particular clinical trial data in which they are interested, and stores the particular clinical trial data in a format relevant to the advanced analysis that they may perform, the custom merged table can be automatically updated in order to provide the user with an up-to-date representation of exactly the clinical trial data that they require in order to carry out their function within, or in associate with a sponsor organization. Relevant methods and systems for retrieving clinical trial data from sources of clinical trial data, and updating custom data tables of clinical trial data are described in detail in U.S. patent application Ser. No. 15/233,847 "Caching Technology for Clinical Data Sources", the entire contents of which is hereby incorporated herein by reference.

Figure 9:
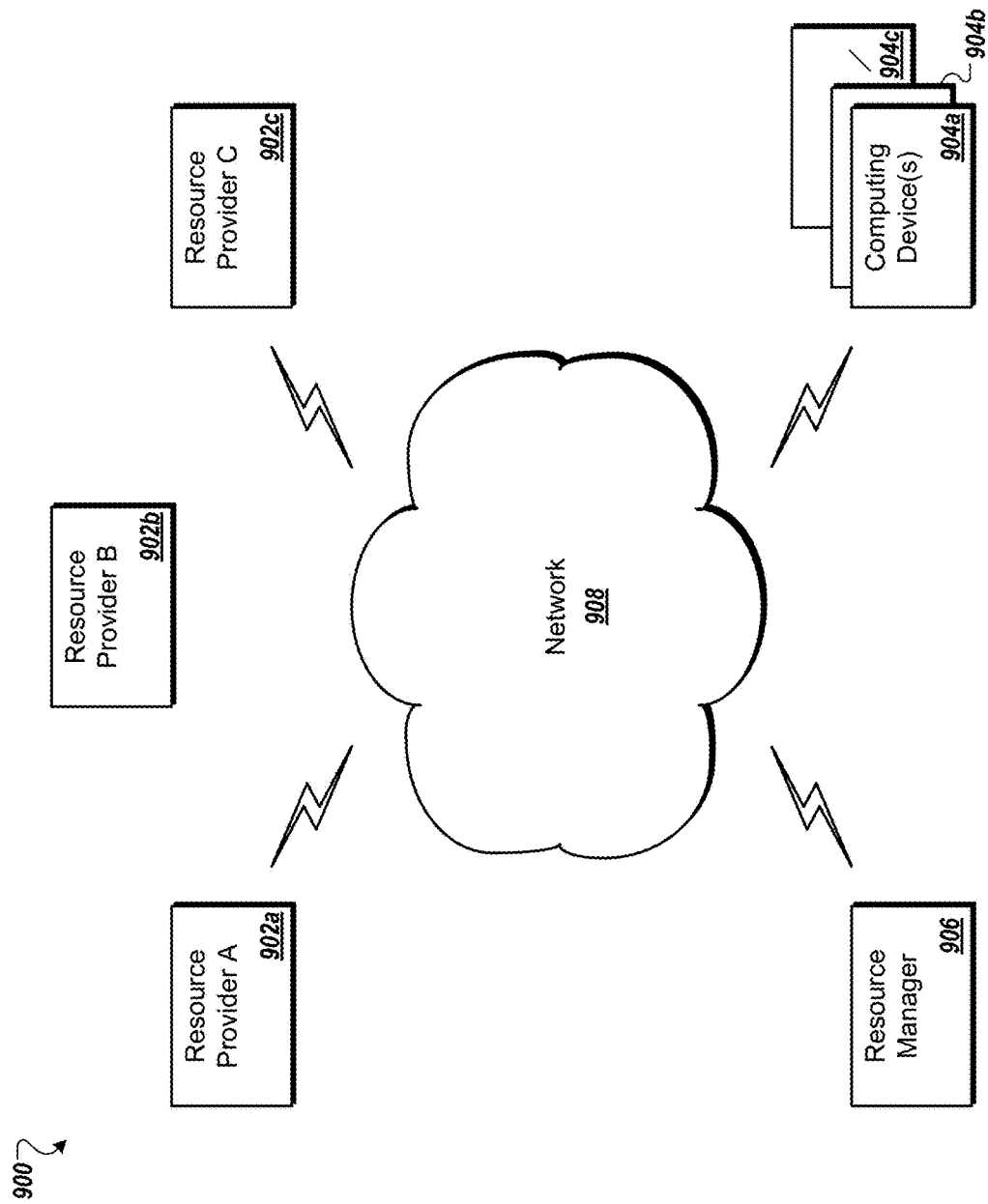
FIG. 9 shows a block diagram of an exemplary cloud computing environment for use in certain embodiments of the invention.

As shown in FIG. 9, an implementation of a network environment 900 for use providing systems and methods for merging datasets from clinical trials as described herein is shown and described. In brief overview, referring now to FIG. 9, a block diagram of an exemplary cloud computing environment 900 is shown and described. The cloud computing environment 900 may include one or more resource providers 902a, 902b, 902c (collectively, 902). Each resource provider 902 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 902 may be connected to any other resource provider 902 in the cloud computing environment 900. In some implementations, the resource providers 902 may be connected over a computer network 908. Each resource provider 902 may be connected to one or more computing device 904a, 904b, 904c (collectively, 904), over the computer network 908.

The cloud computing environment 900 may include a resource manager 906. The resource manager 906 may be connected to the resource providers 902 and the computing devices 904 over the computer network 908. In some implementations, the resource manager 906 may facilitate the provision of computing resources by one or more resource providers 902 to one or more computing devices 904. The resource manager 906 may receive a request for a computing resource from a particular computing device 904. The resource manager 906 may identify one or more resource providers 902 capable of providing the computing resource requested by the computing device 904. The resource manager 906 may select a resource provider 902 to provide the computing resource. The resource manager 906 may facilitate a connection between the resource provider 902 and a particular computing device 904. In some implementations, the resource manager 906 may establish a connection between a particular resource provider 902 and a particular computing device 904. In some implementations, the resource manager 906 may redirect a particular computing device 904 to a particular resource provider 902 with the requested computing resource.

Figure 10:
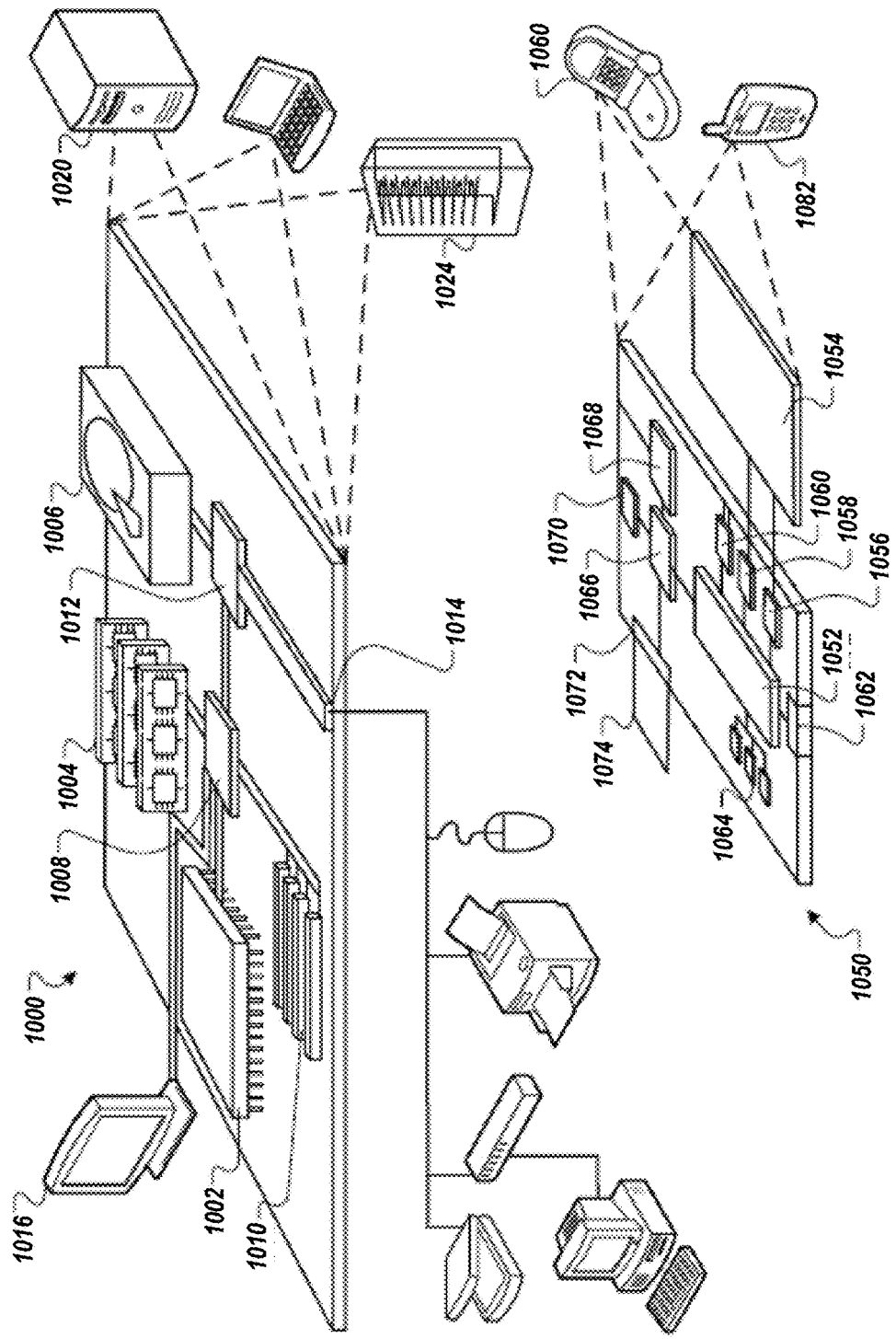
FIG. 10 is a block diagram of a computing device and a mobile computing device for use in certain embodiments of the invention.

FIG. 10 shows an example of a computing device 1000 and a mobile computing device 1050 that can be used to implement the techniques described in this disclosure. The computing device 1000 is intended to represent various forms of digital computers, such as laptops, desktops, workstations, personal digital assistants, servers, blade servers, mainframes, and other appropriate computers. The mobile computing device 1050 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1000 includes a processor 1002, a memory 1004, a storage device 1006, a high-speed interface 1008 connecting to the memory 1004 and multiple high-speed expansion ports 1010, and a low-speed interface 1012 connecting to a low-speed expansion port 1014 and the storage device 1006. Each of the processor 1002, the memory 1004, the storage device 1006, the high-speed interface 1008, the high-speed expansion ports 1010, and the low-speed interface 1012, are interconnected using various busses, and may be mounted on a common motherboard or in other manners as appropriate. The processor 1002 can process instructions for execution within the computing device 1000, including instructions stored in the memory 1004 or on the storage device 1006 to display graphical information for a GUI on an external input/output device, such as a display 1016 coupled to the high-speed interface 1008. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1004 stores information within the computing device 1000. In some implementations, the memory 1004 is a volatile memory unit or units. In some implementations, the memory 1004 is a non-volatile memory unit or units. The memory 1004 may also be another form of computer-readable medium, such as a magnetic or optical disk.

The storage device 1006 is capable of providing mass storage for the computing device 1000. In some implementations, the storage device 1006 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1002), perform one or more methods, such as those described above. The instructions can also be stored by one or more storage devices such as computer- or machine-readable mediums (for example, the memory 1004, the storage device 1006, or memory on the processor 1002).

The high-speed interface 1008 manages bandwidth-intensive operations for the computing device 1000, while the low-speed interface 1012 manages lower bandwidth-intensive operations. Such allocation of functions is an example only. In some implementations, the high-speed interface 1008 is coupled to the memory 1004, the display 1016 (e.g., through a graphics processor or accelerator), and to the high-speed expansion ports 1010, which may accept various expansion cards (not shown). In the implementation, the low-speed interface 1012 is coupled to the storage device 1006 and the low-speed expansion port 1014. The low-speed expansion port 1014, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1000 may be implemented in a number of different forms, as shown in the figure. For example, it may be implemented as a standard server 1020, or multiple times in a group of such servers. In addition, it may be implemented in a personal computer such as a laptop computer 1022. It may also be implemented as part of a rack server system 1024. Alternatively, components from the computing device 1000 may be combined with other components in a mobile device (not shown), such as a mobile computing device 1050. Each of such devices may contain one or more of the computing device 1000 and the mobile computing device 1050, and an entire system may be made up of multiple computing devices communicating with each other.

The mobile computing device 1050 includes a processor 1052, a memory 1064, an input/output device such as a display 1054, a communication interface 1066, and a transceiver 1068, among other components. The mobile computing device 1050 may also be provided with a storage device, such as a micro-drive or other device, to provide additional storage. Each of the processor 1052, the memory 1064, the display 1054, the communication interface 1066, and the transceiver 1068, are interconnected using various buses, and several of the components may be mounted on a common motherboard or in other manners as appropriate.

The processor 1052 can execute instructions within the mobile computing device 1050, including instructions stored in the memory 1064. The processor 1052 may be implemented as a chipset of chips that include separate and multiple analog and digital processors. The processor 1052 may provide, for example, for coordination of the other components of the mobile computing device 1050, such as control of user interfaces, applications run by the mobile computing device 1050, and wireless communication by the mobile computing device 1050.

The processor 1052 may communicate with a user through a control interface 1058 and a display interface 1056 coupled to the display 1054. The display 1054 may be, for example, a TFT (Thin-Film-Transistor Liquid Crystal Display) display or an OLED (Organic Light Emitting Diode) display, or other appropriate display technology. The display interface 1056 may comprise appropriate circuitry for driving the display 1054 to present graphical and other information to a user. The control interface 1058 may receive commands from a user and convert them for submission to the processor 1052. In addition, an external interface 1062 may provide communication with the processor 1052, so as to enable near area communication of the mobile computing device 1050 with other devices. The external interface 1062 may provide, for example, for wired communication in some implementations, or for wireless communication in other implementations, and multiple interfaces may also be used.

The memory 1064 stores information within the mobile computing device 1050. The memory 1064 can be implemented as one or more of a computer-readable medium or media, a volatile memory unit or units, or a non-volatile memory unit or units. An expansion memory 1074 may also be provided and connected to the mobile computing device 1050 through an expansion interface 1072, which may include, for example, a SIMM (Single In Line Memory Module) card interface. The expansion memory 1074 may provide extra storage space for the mobile computing device 1050, or may also store applications or other information for the mobile computing device 1050. Specifically, the expansion memory 1074 may include instructions to carry out or supplement the processes described above, and may include secure information also. Thus, for example, the expansion memory 1074 may be provide as a security module for the mobile computing device 1050, and may be programmed with instructions that permit secure use of the mobile computing device 1050. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 1052), perform one or more methods, such as those described above. The instructions can also be stored by one or more storage devices, such as one or more computer- or machine-readable mediums (for example, the memory 1064, the expansion memory 1074, or memory on the processor 1052). In some implementations, the instructions can be received in a propagated signal, for example, over the transceiver 1068 or the external interface 1062.

The mobile computing device 1050 may communicate wirelessly through the communication interface 1066, which may include digital signal processing circuitry where necessary. The communication interface 1066 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1068 using a radio-frequency. In addition, short-range communication may occur, such as using a Bluetooth®, Wi-Fi™, or other such transceiver (not shown). In addition, a GPS (Global Positioning System) receiver module 1070 may provide additional navigation- and location-related wireless data to the mobile computing device 1050, which may be used as appropriate by applications running on the mobile computing device 1050.

The mobile computing device 1050 may also communicate audibly using an audio codec 1060, which may receive spoken information from a user and convert it to usable digital information. The audio codec 1060 may likewise generate audible sound for a user, such as through a speaker, e.g., in a handset of the mobile computing device 1050. Such sound may include sound from voice telephone calls, may include recorded sound (e.g., voice messages, music files, etc.) and may also include sound generated by applications operating on the mobile computing device 1050.

The mobile computing device 1050 may be implemented in a number of different forms, as shown in the figure. For example, it may be implemented as a cellular telephone 1080. It may also be implemented as part of a smart-phone 1082, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Figure 11:
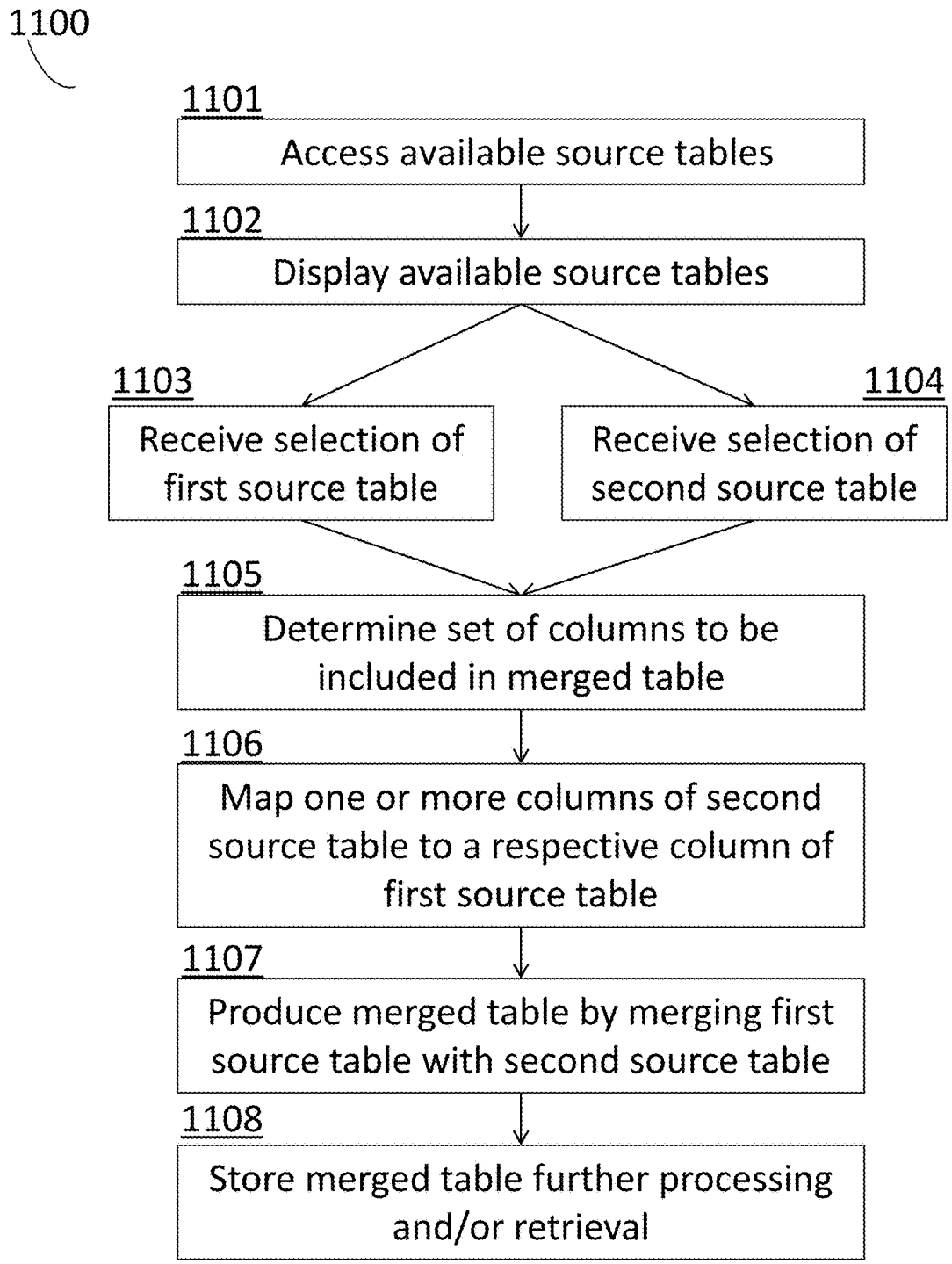
FIG. 11 is a block flow diagram of a process of creating a custom merged table from a first and second source table, according to an illustrative embodiment.

FIG. 11 is a block flow diagram of a process 1100 of creating a custom merged table from a first and second source table, according to an illustrative embodiment. Step 1101 of the process is accessing source tables. In step 1102, the available source tables are displayed on a GUI. A selection of a first source table (e.g. via a user input through the GUI) is received at step 1103. A selection of a second source table (e.g. via a user input through the GUI) is received at step 1104. Step 1105 of the process is determining the set of columns to be included in the final custom merged table. Step 1106 of the process is mapping one or more columns of the second source table to a respective column of the first source table. Step 1107 of the process is merging the first source table with the second source table to produce a custom merged table. Once the custom merged table is created, the process stores the merged table for further processing and/or retrieval (e.g. by a client application) at step 1108.

Figure 12:
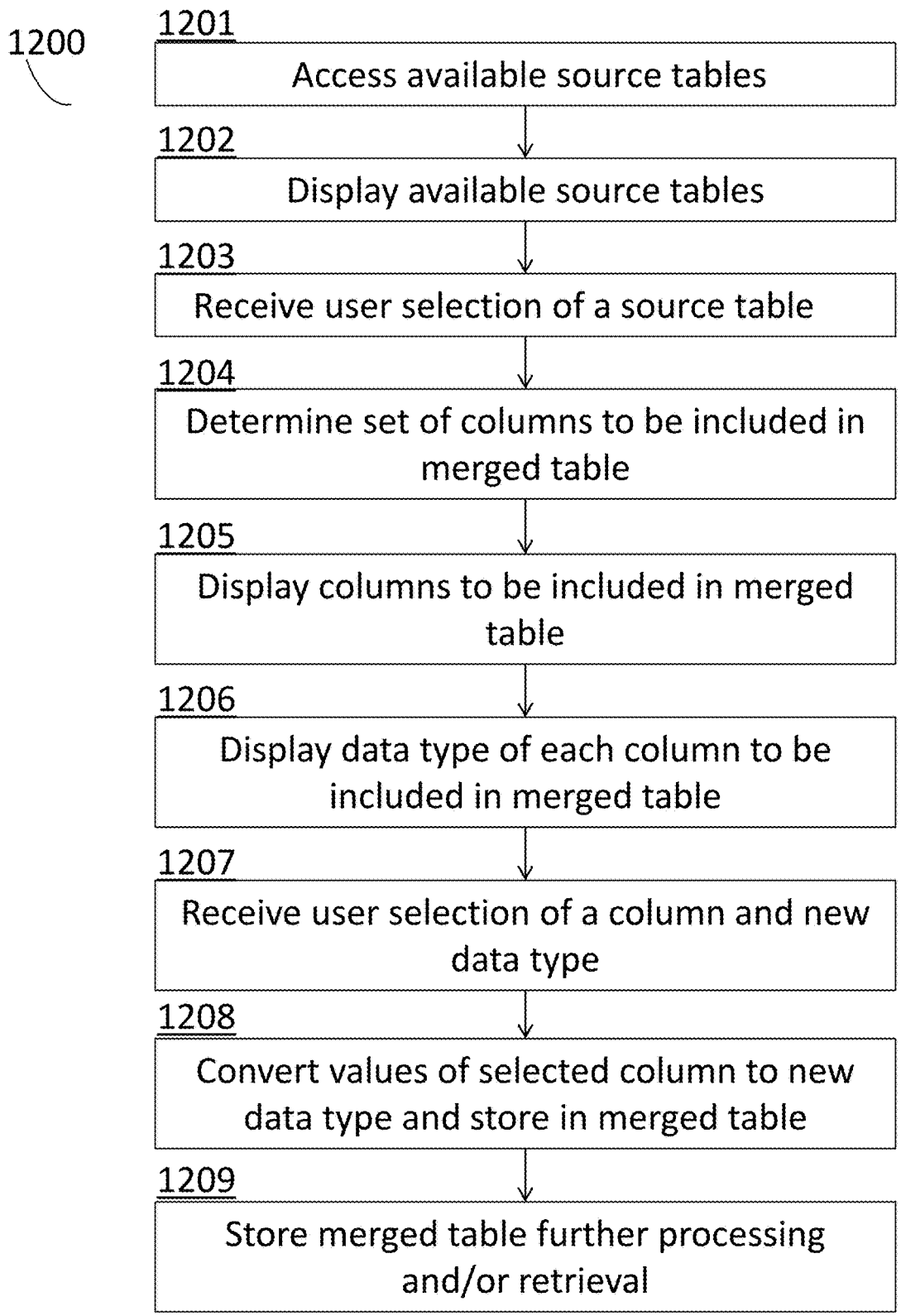
FIG. 12 is a block flow diagram for changing the data type of values stored in one or more columns of a source table of clinical trial data, according to an illustrative embodiment.

FIG. 12 is a block flow diagram of a process 1200 for changing the data type of values stored in one or more columns of a source table of clinical trial data, according to an illustrative embodiment. Step 1201 of the process is accessing available source tables. In step 1202, the available source tables are displayed on a GUI. A selection of a source table (e.g. via a user input through the GUI) is received at step 1203. The process determines the set of columns to be included in a custom merged table 1204, and displays the columns via the GUI 1205. In step 1206, the process displays the initial data types of each column to be included in the merged table. In step 1207 the process receives a user selection of a column and a new data type. In step 1208, the process creates a custom merged table by, for each column to be included in the merged table, storing the values of the corresponding column of the source table in the respective column of the merged table, wherein storing the values of the column of the source table corresponding to the selected column comprises converting the values of the column of the source table corresponding to the selected column to the new data type, and storing the converted values in the merged table. At step 1209, the generated merged table is stored for further processing and/or retrieval (e.g. by a client application).

In some implementations, the modules (e.g. data table import module, table merge/unmerge module, column mapping/unmapping module, data type conversion module) described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. In view of the structure, functions and apparatus of the systems and methods described here, in some implementations, systems and methods for merging datasets from clinical trials are provided. Given the description in this specification, other implementations of systems and methods for merging datasets from clinical trials incorporating the concepts of this disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for merging two or more source tables of clinical trial data associated with one or more clinical studies to produce a custom merged table via a graphical user interface (GUI), the method comprising:

receiving, by a processor of a computing device, a user selection of a first source table from a displayed list of available source tables, wherein the first source table comprises n rows and comprises first information entered via a first clinical form that corresponds to a first study protocol, and wherein the first information corresponds to one or more first fields of the first clinical form;

receiving, by the processor, a user selection of a second source table from the list of available source tables, wherein the second source table comprises m rows and comprises second information entered via a second clinical form that is different from the first clinical form and corresponds to a second study protocol that is different from the first study protocol, and wherein the second information corresponds to one or more second fields of the second clinical form that are different from the one or more first fields of the first clinical form;

determining, by the processor, a set of columns to be included in a merged table, wherein each column in the set of columns corresponds to either a column of the first source table or a column of the second source table, by:

populating a set of initial columns of the merged table based on the columns in the first source table;

automatically mapping each of one or more columns of the second source table to a respective column in the first source table;

displaying, in a first region of the GUI, a name of the first source table and names of each of the columns in the first source table;

displaying, in a second region of the GUI adjacent to the first region, a name of the second source table and names of each of the columns in the second source table that are mapped to a respective column in the first source table;

displaying, in a third region of the GUI separate from the first region and the second region, a name of each of the columns in the second source table that are not mapped to any of the columns in the first source table;

receiving a user selection of at least one unmapped column of the second source table via the third region of the GUI; and adding the selected unmapped column of the second source table to the set of columns to be included in the merged table;

merging, by the processor, the first source table with the second source table to produce the merged table, wherein merging the first source table with the second source table comprises:

for each column in the set of columns to be included in the merged table that corresponds to a column in the first source table to which a column of the second source table is mapped:
  selecting, based on a difference between a first data type of the n values from the column in the first source table and a second data type of the m values from the column in the second source table, a third data type;
  converting the n values from the column in the first source table to the third data type;
  storing each of the converted n values from the column in the first source table in consecutive rows 1 through n of a corresponding column in the merged table;
  converting the m values from the column in the second source table to the third data type; and
  storing each of the converted m values from the column in the second source table that is mapped to the column of the first source table in consecutive rows (n+1) through (n+m) immediately following rows 1 through n of the corresponding column in the merged table; and
storing, by the processor, the merged table for further processing and/or retrieval by a client application.

2. The method of claim 1, wherein determining the set of columns to be included in the merged table further comprises:
  identifying the columns in the first source table; and
  for each identified column of the first source table, adding a corresponding column to the set of columns to be included in the merged table, such that each column in the set of columns to be included in the merged table initially corresponds to a column of the first source table.

3. The method of claim 1, wherein automatically mapping one or more columns of the second source table to a respective column in the first source table comprises:
  determining, by the processor, that a name of a column of the first source table matches a name of a column of the second source table; and
  mapping, by the processor, the matching column of the second source table to the matching column of the first source table.

4. The method of claim 1, wherein merging the first source table with the second source table comprises:
  for each column in the set of columns to be included in the merged table that corresponds to a column in the first source table to which no column in the second source table is mapped:
    storing each of the converted n values from the column in the first source table in n consecutive rows 1 through n of a corresponding column of the merged table, leaving immediately following consecutive rows (n+1) through (n+m) blank; and
  for each column in the set of columns to be included in the merged table that corresponds to a column in the second source table that is not mapped to a column in the first source table:
    storing each of the converted m data values from the column in the second source table in consecutive rows (n+1) through (n+m) of a corresponding column of the merged table immediately following rows 1 through n, leaving rows 1 through n blank.

5. The method of claim 1, comprising at least one of:
  (i) receiving, by the processor, a user selection of a column in the second source table that is not previously mapped to any of the columns in the first source table, and mapping the selected column of the second source table to a selected column in the first source table; or
  (ii) receiving, by the processor, a user selection of a column in the second source table that is mapped to a respective column the first source table, and unmapping the selected column of the second source table from the respective column of the first source table.

6. The method of claim 1, comprising:
  in a designated location of the GUI, displaying a name of each column in the set of columns to be included in the merged table;
  receiving, by the processor, a user selection of a column in the set of columns to be included in the merged table to be removed from the merged table; and
  removing the selected column from the set of columns to be included in the merged table.

7. The method of claim 1, comprising:
  displaying, in a designated location of the GUI, a name of each column in the set of columns to be included in the merged table, along with an indication of a corresponding data type, wherein the corresponding data type is a data type that will be used to store values in the column.

8. The method of claim 1, wherein selecting the third data type comprises:
  receiving a user selection of the third data type from a list of data types.

9. The method of claim 1, wherein the first source table comprises data from a first study event, and wherein the second source table comprises data from a second study event that is distinct from the first study event.

10. The method of claim 1, wherein the first source table comprises data from a first clinical study, and wherein the second source table comprises data from a second clinical study that is distinct from the first clinical study.

11. The method of claim 1, wherein each table of the available source tables comprises data recorded using a different form, wherein each form is a pre-defined template that identifies a set of data to be recorded during a study event of a clinical trial.

12. The method of claim 1, wherein each table of the available source tables comprises one or more form entries, each form entry comprising a set of clinical trial data recorded for a particular subject, at a particular study event, and using a particular form comprising a list of predefined fields for which data is collected.

13. The method of claim 1, wherein at least one of the first source table and the second source table comprises operational data.

14. The method of claim 13, wherein the operational data comprises at least one member selected from the group consisting of an audit record, a query, a comment, and a signature.

15. The method of claim 13, wherein the operational data comprises an audit record.

16. The method of claim 13, wherein the operational data comprises an electronic signature.

17. The method of claim 1, comprising automatically updating, by the processor, the merged table to reflect updates to the clinical trial data.

18. A method for changing a data type of values stored in one or more columns of a source table of clinical trial data associated with one or more clinical studies via a graphical user interface (GUI), the method comprising:
  (a) accessing, by a processor of a computing device, a plurality of available source tables, wherein each table of the plurality of available source tables comprises data recorded using a different clinical form, wherein each clinical form is a pre-defined template that corresponds to a respective study protocol and identifies a set of data to be recorded during a study event of a clinical study, and wherein each clinical form comprises one or more fields different from another clinical form;

(b) providing, by the processor and for display on the GUI a list of available source tables;

(c) receiving, by the processor, a user selection of a source table from the list of available source tables;

(d) determining, by the processor, a set of columns to be included in a merged table, wherein each column in the set of columns corresponds to a column of the source table;

(e) displaying, by the processor, in a first designated location of the GUI a name of each of the columns to be included in the merged table;

(f) for each column to be included in the merged table, displaying, by the processor, an indication of a data type of the respective column;

(g) receiving, by the processor, a user selection of a column to be included in the merged table;

(h) determining, by the processor and based on a current data type of the selected column, a new data type for the selected column;

(i) for each column to be included in the merged table, storing, by the processor, the values of the corresponding column of the source table in the respective column of the merged table, wherein storing the values of the column of the source table corresponding to the selected column comprises converting the values of the column of the source table corresponding to the selected column to the new data type, and storing the converted values in the merged table; and (j) storing, by the processor, the merged table for further processing and/or retrieval by a client application.

19. The method of claim 18, wherein determining the set of columns to be included the merged table comprises identifying the columns in the source table, and for each identified column of the source table, adding a corresponding column to the set of columns to be included in the merged table, such that each column in the set of columns to be included in the merged table initially corresponds to a column of the source table.

20. The method of claim 18, comprising:
in a designated location of the GUI, displaying a name of each column in the set of columns to be included in the merged table;
receiving, by the processor, a user selection of a column in the set of columns to be included in the merged table to be removed from the merged table; and
removing the selected column from the set of columns to be included in the merged table.

21. The method of claim 18, wherein each table of the plurality of available source tables comprises one or more form entries, each form entry comprising a set of clinical trial data recorded for a particular subject, at a particular study event, and using a particular clinical form comprising a list of predefined fields for which data is collected.

22. The method of claim 18, wherein the source table comprises operational data.

23. The method of claim 22, wherein the operational data comprises at least one member selected from the group consisting of an audit record, a query, a comment, and a signature.

24. The method of claim 22, wherein the operational data comprises an audit record.

25. The method of claim 22, wherein the operational data comprises an electronic signature.

26. The method of claim 18, comprising automatically updating, by the processor, the merged table to reflect updates to the clinical trial data.

27. An apparatus configured to merge two or more source tables of clinical trial data associated with one or more clinical studies to produce a merged table via a graphical user interface (GUI), the apparatus comprising:
one or more processors; and
memory storing instructions that, when executed by the one or more processors, cause the apparatus to:
receive a user selection of a first source table from a displayed list of available source tables, wherein the first source table comprises n rows and comprises first information entered via a first clinical form that corresponds to a first study protocol, and wherein the first information corresponds to one or more first fields of the first clinical form;
receive a user selection of a second source table from the list of available source tables, wherein the second source table comprises m rows and comprises second information entered via a second clinical form that is different from the first clinical form and corresponds to a second study protocol that is different from the first study protocol, and wherein the second information corresponds to one or more second fields of the second clinical form that are different from the one or more first fields of the first clinical form;
populate a set of initial columns of the merged table based on the columns in the first source table;
automatically map each of one or more columns of the second source table to a respective column in the first source table;
display, in a first region of the GUI, a name of the first source table and names of each of the columns in the first source table;
display, in a second region of the GUI adjacent to the first region, a name of the second source table and names of each of the columns in the second source table that are mapped to a respective column in the first source table;
display, in a third region of the GUI separate from the first region and the second region, a name of each of the columns in the second source table that are not mapped to any of the columns in the first source table;
receive a user selection of at least one unmapped column of the second source table via the third region of the GUI;
determine a set of columns to be included in the merged table, wherein the set of columns comprises each column of the first source table and the selected unmapped column of the second source table;
merge the first source table with the second source table to produce the merged table, wherein the instructions cause the apparatus to merge each column in the set of columns to be included in the merged table that corresponds to a column in the first source table to which a column of the second source table is mapped by causing the apparatus to:
select, based on a difference between a first data type of the n values from the column in the first source table and a second data type of the m values from the column in the second source table, a third data type;

convert the n values from the column in the first source table to the third data type;

store each of the n values from the column in the first source table in consecutive rows 1 through n of a corresponding column in the merged table;

convert the m values from the column in the second source table to the third data type; and store each of the m values from the column in the second source table that is mapped to the column of the first source table in consecutive rows (n+1) through (n+m) immediately following rows 1 through n of the corresponding column in the merged table; and store the merged table for further processing or retrieval by a client application.

28. The apparatus of claim 27, wherein the instructions, when executed by the one or more processors, further cause the apparatus to select the third data type by:

receiving a user selection of the third data type from a list of data types.

29. The apparatus of claim 27, wherein the instructions comprise a plug-in software module for the client application.

* * * * *